United States Patent [19]
Hamilton et al.

[11] Patent Number: 5,990,131
[45] Date of Patent: *Nov. 23, 1999

[54] HETEROCYCLIC THIOESTERS AND KETONES

[75] Inventors: Gregory S. Hamilton, Catonsville; Jia-He Li, Cockeysville, both of Md.

[73] Assignee: Gpi Nil Holdings Inc., Wilmington, Del.

[*] Notice: This patent is subject to a terminal disclaimer.

[21] Appl. No.: 08/904,461

[22] Filed: Aug. 1, 1997

Related U.S. Application Data

[63] Continuation-in-part of application No. 08/721,765, Sep. 25, 1996.

[51] Int. Cl.$^6$ ........................ A61K 31/445; C07D 211/06
[52] U.S. Cl. ...................... 514/330; 546/226; 548/533; 548/540; 514/422; 514/423
[58] Field of Search .................... 548/533, 540; 514/422, 423, 330; 546/226

[56] References Cited

U.S. PATENT DOCUMENTS

| | | | |
|---|---|---|---|
| 4,310,461 | 1/1982 | Krapcho et al. | 260/326.2 |
| 4,374,829 | 2/1983 | Harris et al. | 424/177 |
| 4,390,695 | 6/1983 | Krapcho et al. | 544/130 |
| 4,531,964 | 7/1985 | Shimano et al. | 71/92 |
| 4,574,079 | 3/1986 | Gavras et al. | 424/1.1 |
| 4,578,474 | 3/1986 | Krapcho et al. | 546/188 |
| 4,593,102 | 6/1986 | Shanklin, Jr. | 546/216 |
| 4,766,110 | 8/1988 | Ryan et al. | 514/19 |
| 4,808,573 | 2/1989 | Gold et al. | 514/19 |
| 4,818,749 | 4/1989 | Gold et al. | 514/19 |
| 5,147,877 | 9/1992 | Goulet | 514/291 |
| 5,166,317 | 11/1992 | Wallace et al. | 530/350 |
| 5,192,773 | 3/1993 | Armistead et al. | 514/315 |
| 5,215,969 | 6/1993 | Springer et al. | 514/21 |
| 5,232,923 | 8/1993 | Fukazawa et al. | 514/237.5 |
| 5,252,579 | 10/1993 | Skotnicki et al. | 514/291 |
| 5,294,603 | 3/1994 | Rinehart | 514/10 |
| 5,319,098 | 6/1994 | Burbaum et al. | 548/533 |
| 5,330,993 | 7/1994 | Armistead et al. | 514/323 |
| 5,359,138 | 10/1994 | Takeuchi et al. | 562/567 |
| 5,385,918 | 1/1995 | Connell et al. | 514/330 |
| 5,414,083 | 5/1995 | Hackl et al. | 544/130 |
| 5,424,454 | 6/1995 | Burbaum et al. | 548/533 |
| 5,447,915 | 9/1995 | Schreiber et al. | 514/18 |
| 5,516,797 | 5/1996 | Armistead et al. | 514/548 |
| 5,543,423 | 8/1996 | Zelle et al. | 514/332 |
| 5,717,092 | 2/1998 | Armistead et al. | 544/129 |

FOREIGN PATENT DOCUMENTS

| | | |
|---|---|---|
| 12401 | 6/1980 | European Pat. Off. . |
| 48159 | 3/1982 | European Pat. Off. . |
| 48159A2 | 3/1982 | European Pat. Off. . |
| 50800 | 5/1982 | European Pat. Off. . |
| 73143 | 3/1983 | European Pat. Off. . |
| 88350 | 9/1983 | European Pat. Off. . |
| 196841 | 10/1986 | European Pat. Off. . |
| 260118 | 3/1988 | European Pat. Off. . |
| 333174 | 9/1989 | European Pat. Off. . |
| 352000 | 1/1990 | European Pat. Off. . |
| 378318 | 7/1990 | European Pat. Off. . |
| 405994 | 1/1991 | European Pat. Off. . |
| 419049 | 3/1991 | European Pat. Off. . |
| 468339 | 1/1992 | European Pat. Off. . |
| 572365 | 12/1993 | European Pat. Off. . |
| 652229 | 5/1995 | European Pat. Off. . |
| 3508251 | 9/1986 | Germany . |
| 3931051 | 3/1990 | Germany . |
| 4015255 | 11/1991 | Germany . |
| 04149166 | 5/1992 | Japan . |
| 05178824 | 7/1993 | Japan . |
| 9207782 | 4/1993 | South Africa . |
| 2247456 | 3/1992 | United Kingdom . |
| WO8809789 | 12/1988 | WIPO . |
| WO9012805 | 11/1990 | WIPO . |
| WO9104985 | 4/1991 | WIPO . |
| WO9113088 | 9/1991 | WIPO . |
| WO9200278 | 1/1992 | WIPO . |
| WO9203472 | 3/1992 | WIPO . |
| WO9204370 | 3/1992 | WIPO . |
| WO9216501 | 10/1992 | WIPO . |
| WO9218478 | 10/1992 | WIPO . |
| WO9219593 | 11/1992 | WIPO . |
| WO9219745 | 11/1992 | WIPO . |
| WO9221313 | 12/1992 | WIPO . |
| WO9307269 | 4/1993 | WIPO . |
| WO9313066 | 7/1993 | WIPO . |
| WO9323548 | 11/1993 | WIPO . |
| WO9325546 | 12/1993 | WIPO . |
| WO9405639 | 3/1994 | WIPO . |
| WO9407858 | 4/1994 | WIPO . |
| WO9413629 | 6/1994 | WIPO . |
| WO9512572 | 5/1995 | WIPO . |
| WO9524385 | 9/1995 | WIPO . |
| WO9526337 | 10/1995 | WIPO . |
| WO9535308 | 12/1995 | WIPO . |
| WO9535367 | 12/1995 | WIPO . |
| WO9606097 | 2/1996 | WIPO . |
| WO9615101 | 5/1996 | WIPO . |
| WO9617816 | 6/1996 | WIPO . |
| WO 9641609 | 12/1996 | WIPO . |
| WO 97/36869 | 10/1997 | WIPO . |

OTHER PUBLICATIONS

Rao, A.V. Rama et al., "Studies directed towards the synthesis of immunosuppressive agent FK–506: synthesis of the entire bottom half," Tetrahedron Lett., 1991, 32(9), 1251–4.

Fisher, Matthew et al., "On the remarkable propensity for carbon–carbon bond cleavage reactions in the C(8)–C(10) region of FK–506," J. Org. Chem., 1991, 56(8), 2900–7.

(List continued on next page.)

Primary Examiner—John Kight
Assistant Examiner—Charanjit S. Aulakh
Attorney, Agent, or Firm—Nath & Associates; Gary M. Nath; Lee C. Heiman

[57] ABSTRACT

This invention relates to neurotrophic low molecular weight, small molecule heterocyclic thioesters and ketones having an affinity for FKBP-type immunophilins, and their use as inhibitors of the enzyme activity associated with immunophilin proteins, particularly peptidyl-prolyl isomerase, or rotamase, enzyme activity.

58 Claims, 4 Drawing Sheets

OTHER PUBLICATIONS

Linde, Robert G. et al., "Straightforward synthesis if 1,2,3–tricarbonyl systems," J. Org. Chem., 1991, 56(7), 2534–8.

Hayward, C.M. et al., "An application of the Suarez reation to the regiospecific synthesis of the $C_{28}$–$C_{42}$ segment of rapamycin,", 1993, 3989–92.

Waldmann, Herbert, "Proline benzyl ester as chiral auzilary in Barbier–type reactions in aqueous solution," 1990, Synlett, 10, 627–8.

Gold, Bruce G. et al., "Regulation of aberrant neurofilament phosophorylation in neuronal periokarya. IV. Evidence for the involvement of two signals," Brain Search, 626 (1993) 23–30.

Hauske, James R. et al., "Design and Synthesis of Novel FKBP Inhibitors," J. Med. Chem., 1992, 35, pp. 4284–4296.

Holt, Dennis A. et al., "Structure Acitivity Studies of Non-macrocyclic Rapamycin Derivatives," Bioorganic & Medical Chemistry Letters, 1993, vol. 3, No. 10, pp. 1977–1980.

Yamashita, Dennis S. et al., "Design Synthesis and Evaluation of Dual Domain FKBP Ligands," Bioorganic & Medicinal Chemistry Letters, 1994, vol. 3, No. 2, pp. 325–328.

Teague, Simon J. et al., "Synthesis and Study of a Non Macrocyclic FK506 Derivative," Bioorganic & Medicinal Chemistry Letters, 1994, vol. 4, No. 13, pp. 1581–1584.

Luengo, Juan I. et al. "Synthesis and Structure–Activity Relationships of Macrocyclic FKBP Ligands," Bioorganic & Medicinal Chemistry Letters, 1994, vol. 4, No. 2, pp. 321–324.

Holt, Dennis A. et al., "Structure–Activity Studies of Synthetic FKBP Ligands as Prptidyl–Prolyl Isomerase Inhibitors," Bioorganic & Medicinal Chemistry Letters, 1994, vol. 4, No. 2, pp. 315–320.

Teague, Simon J. et al. "The Affinity of the Excised Binding Domain of the FK–506 for the Immunophilin FKBP12," Bioorganic & Medicinal Chemsitry Letters, 1993, vol. 3, No. 10, pp. 1947–1950.

Caffrey, Moya V. et al. "Synthesis and Evaluation of Dual Domain Macrocyclic FKBP12 Ligands," Bioorganic & Medicinal Chemsitry Letters, 1994, vol. 4, No. 21, pp. 2507–2510.

Birkenshaw, Timothy N. et al. "Synthesis FKBP12 Ligands. Design and Synthesis of Pyranose Replacements," Bioorganic & Medicinal Chemsitry Letters, 1994, vol. 4, No. 21, pp. 2501–2506.

Holt, Dennis A. et al. "Design, Synthesis, and Kinetic Evaluation of High–Affinity FKBP Ligands and the X–ray Crystal Structures of their Complexes with FKBP12", J. Am. Chem. Soc., 1993, 115, pp. 9925–9938.

Wang, Gary T. et al. "Synthesis and FKBP Binding of Small Molecule Mimics of the Tricarbonyl Region of FK506," Bioorganic & Medicinal Chemistry Letters, 1994, vol. 4, No. 9, pp. 1161–1166.

Snyder, Solomon H. and Sabatini, David M., "Immunophilins and the Nervous System," Nature Medicine, 1995, vol. 1, No. 1, pp. 32–37.

Egbertson, M., and Danishefsky, S., "A synthetic route to the tricarbonyl region of FK–506," J. Org. Chem., 1989, 54(1), 11–12.

Williams, D.R. and Benbow, J.W., "Synthesis of the $\alpha,\beta$ diketo amide segment of the novel immunosuppresive FK506," J. Org. Chem., 1988, 53(191), 4643–4.

Kocienski, P. et al., "A synthesis of the C(1)–C(15) segemnt of tsukubaenolide (FK506)," Tetrahedron Lett., 1988, 29(35), 4481–4.

Tanaka, H. et al., "Structure of FK506, a novel immunosuppressant isolated from Streptomyces," J. Am. Chem. Soc., 1987, 109(16), 5031.3.

Marshall, J.A. et al., "Convenient synthesis of dioxopiperazines via aminolysis of .alpha.–(pyruvylamino) esters," Synth. Commun., 1975, 5(3), 237–44.

Stocks, Michael J. et al. "The Contriction to Binding of the Pyranoside Substituents in the Excised Binding Domain of FK–506," Bioorganic & Medicinal Chemistry Letters, 1994, vol. 4, No. 12, pp. 1457–1460.

Haeusler, Johannes and Schmidt, Ulrich, "Amino acids and peptides. IX. Pyruvoyl amino acids," Chem. Ber., 1974, 107(1), 145–51. (German).

Hearn, Walter R., and Worthington, Robert E., "L–Proline–N–oxalic anhydride," J. Org. Chem., 1967, 32(12), 4072–4.

Steffan, Robert J. et al., "Base catalyzed degradation of rapamycin," Tetrahedron Lett., 1993, 34(23), 3699–702.

Nicolau, K.C. et al., "Total Synthesis of rapamycin," J. Am. Chem. Soc., 1993, 115(10), 4419–20.

Hayward, C.M. et al., "Total synthesis of rapamycin via a novel titanium–mediated aldol macrocyclization reaction," J. Am. Chem. Soc., 1993, 115(20), 9345–6.

Yohannes, Daniel et al. "Degradation of rapamycin: synthesis of a rapamycin–derived fragment containing the tricarbonyl and triene sectors," Tetrahedron Lett., 1993, 34(13), 2075–8.

Luengo, J. et al., "Studies on the chemistry of rapamycin: novel transformation under Lewis–acid catalysis," Tetrahedron Lett., 1993, 34(6), 991–4.

Yohannes, Daniel et al., "Degradation of rapamycin: retrieval of major intact subunits," Tetrahedron Lett., 1992, 33(49), 7469–72.

Hovarth, R. et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, Ene Reactions of Chiral $\alpha$–Ketoesters," J. Chem. Soc., Chem Commun., 1983, 802.

Ando, Takao et al., "Formation of Crossed Phenzine from the reaction between Tetra–p–anisyl– and Tetra–p–tolyl–hydrazines in Liquid Sulphur Dioxide," Chem. Comm., S. Chem. Comm., 1975, 989.

Kino, Toru et al., "FK–506, A novel immunosuppressant isolated from A Streptomyces," J. of Antibiotics, 1987, 40(9), 1249–55.

Goulet, Mark T. and Boger, Joshua, "Degradative studies on the tricarbonyl containing macrolide rapamycin," Tetrahedron Lett., 1991, 32(45), 6454.

Goulet, Mark T. et al., "Construction of the FK–506 analog from rapamycin–derived materials," Tetrahedron Lett., 1991, 32(36), 4627–30.

Armistead, D.M. et al., "Design, synthesis and structure of non–macrocyclic inhibitors of FKBP12, the major binding protein for the immunosuppressant FK506," Acta Crystallogr. 1995, D51(4), 522–8.

Luengo, J. et al., "Structure–activity studies of rapamycin analogs:evidence that the C–7 methodoxy group is part of the effector domain and positioned at the FKBP:12–FRAP interface," Chem. Biol., 1995, 2(7), 471–81.

Furber, Mark, "FKBP–12–ligand–calceineurin interactions: analogs of SBL506," J. Am. Chem. Soc., 1995, 117(27), 7267–8.

Wang CP et al., "A high performance liquid chromatographic method for the determination of rapamycin (sirolamus) in the rat serum, plasma, and blood and in monkey serum," J. Liq. Chromatogr., 1995, 18(9), 1801–8.

Chakraborty, TK et al., "Design and Synthesis of a rapamycin–based high affinity binding FKBP12 ligand," Chem. Biol., 1995, (2)3, 157–61.

Smith, A.B. et al., "Total synthesis of rapamycin and demethoxyrapamycin," J. Am. Chem. Soc., 1995, 117(19), 5407–8.

Baumann, K. et al., "Synthesis and oxidative cleavage of the major equilibrium products of ascomycin and FK 506," Tetrahedron Lett., 1995, 26(13), 2231–4.

Nelson, F. et al., "A novel ring contraction of rapamycin," Tetrahedron Lett., 1994, 35(41), 7557–60.

Dawson, T.M. et al., "The immunophilins, FK506 binding and cyclophilin, are discretely localized in the brain: relationship to calcineurin," Neuroscience, 1994, 62(2), 569–80.

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Stocks, M. et al., "The contribution to the binding of the pyranoside sustituents in the excised binding domain of FK–506," Bioorg. Med. Chem. Lett., 1994, 4(12), 1457–60.

Steiner, J.P. et al., "Nonimmunosuppressive Ligands for Neuroimmunophilins Promote Nerve Extension In Vitro and In Vivo," Soc. For Neuroscience Abstracts, 1996, 22, 297.13.

Lyons, W. Ernest et al., "Neronal Regeneration Enhances the Expression of the Immunophilin FKBP–12," The Journal of Neuroscience, 1995, 15, 2985–94.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Rao, A.V. Rama and Desibhatla, Vidyanand, "Studies directed towards the synthesis of rapamycin: stereoselective synthesis of C–1 to C–15 segment," Tetrahedron Lett., 1993, 34(44), 7111–14.

Andrus, Merrit B., "Structure–based design of an acyclic ligand that bridges FKBP12 and calcineurin," J. Am. Chem. Soc., 1993, 115(2), 10420–1.

Luengo, Juan I. et al., "Efficient removal of pipecolinate from rapamycin and FK506 by reaction with tetrabutylammonium cyanide," Tetrahedron Lett., 1993, 34(29), 4599–602.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Holt, Dennis A. et al., "Structure–activity of synthetic FKBP ligands as peptidyl–prolyl isomerase inhibitors," Bioorg. Med. Chem. Lett., 1994, 4(2), 315–20.

Karle, Isabella L. et al., "Conformation of the oxalamide group in retro–bispeptides. Three crystal structures." Int. J. Pept. Protein Res., 1994, 43(2), 160–5.

Kaczmar, et al., "Darstellung verscheider Schlangenkafig–Polyelektrolyte auf der Basis von Polyacrylamiden und einem Anionenaustauscher," Makromol. Chem., 1976, 177, 1981–9. (German).

Steiner, Jospeh P. et al., "High brain densities of the immunophilin FKBP colocalized with calcineurin," Nature Lett., 1992, 358, 584–7.

Pattenden, Gerald and Tnkard, Mark, "Facile Synthesis of the tricarbonyl subunit in the immunosuppresant rapamycin," Tetrahedron Lett., 1993, 34(16), 2677–80.

Furber, M. et al., "Studies relating to the immunosuppressive activity of FK506," Tetrahedron Lett., 1993, 34(8), 1351–4.

Ranganathan, Darshan et al., "Oxalopeptides as core motifs for protein design," J. Chem. Soc., 1993, (1), 92–4.

Dawson, Ted M. et al. "Immunosuppressant FK506 enhances phosphorylation of nitric oxide synthase and protects against glutamate neurotoxicity," Proc. Natl. Acad. Sci. USA, 1993, 90, 9808–12.

Cunliffe, C. Jane et al., "Novel inhibitors of proplyl 4–hydroxylase. 3. Inhibition by the substrate analog N–oxaloglycine and its derivatives," J. Med. Chem., 1992, 35(14), 2652–8.

Waldmann, Herbert, "Amino acid esters as chiral auxilaries in Barbier–type reactions in aqueous solutions," Liebigs Ann. Chem., 1991, (12), 1317–22. (German).

Krit, N.A. et al., "Impact of the nature of alkyl radical on the biological activity of N–carboxyalkyl dipeptides," Khim.–Farm. Zh., 1991, 25(7), 44–6. (Russian).

Blaschke et al., Chemical Abstracts, 1974, 84, 78405k.

Caufield, Craig E. and Musser, John H., Annual Reports in Medicinal Chemistry, Johns (Ed.), Academic Press, Inc., Chapter 21, 195–204, 1989.

Effenberger F. et al., "Diastereoselective addition of benzenesulfenyl chloride to 1–acryloylproline esters," Chemical Abstracts, 1989, 10, 778–9.

Nakatsuta. M. et al. "Total Synthesis of FK506 and an FKBP Probe Reagent, ($C_8$, $C_{9-13}C_2$)–FK–506," J. Am. Chem. Soc., 1990, 112 (14), 5583–90.

Shu, A. et al., "Synthesis of I–125 labeled photoaffinity rapamycin analogs," J. Labelled Compd. Radiopharm., 1996, 38(3), 277–37.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cyclosporin hybrid marcocycles," Bioorg. Med. Chem. Lett., 1995, 5(20), 2341–6.

Stocks, M. et al., "macrocyclic ring closures employing the intramolecular Heck reaction," Tetrahedron Lett., 1995, 36(36), 6555–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Chakaraborty, Tushar K., "Studies towards the development of cyclic peptide–based analogs of macrolide immunosuppresants," Pure Appl. Chem., 1996, 68(3), 565–568.

Ponticelli, Claudio, "Treatment of the Nephrotic Syndrome with Cyclosporin A," J. of Autoimmunity, 1992, 5, 315–24.

Tindall, Richard S.A., "Immunointervention with Cyclosporin A in autoimmune Neurological Disorders," J.of Autoimmunity, 1992, 5, 301–313.

Tugwell, Peter, "Cyclosporin in the Treatment of Rheumatoid Arhtritis", J. of Autoimmunity, 1992, 5, 231–40.

Fry, Lionel, "Psoriasis: Immunopathology and Long–term Treatment with Cyclosporin," J. of Autoimmunity, 1992, 5, 277–83.

Feutran, Gilles, "The Optimal use of Cyclosporin o in Autoimmune Disease," J. of Autoimmunity, 1992, 5, 183–95.

Slee, Deborah H. et al., "Selectivity in the Inhibition of HIV and FIV Protease: Inhibitory and Mechanistic Studies of Pyrrolidine–Containing α–Keto Amide and Hydroxyethylamine Core Structures," J. Am. Chem. Soc., 1995, 117(48), 1187–78.

Nicolau, K.C. et al., "Total synthesis of rapamycin," Che.— Eur. J., 1995, 1(5), 318–33.

Munoz, Benito et al., "α–ketoamide Phe–Pro isostere as a new core structure for the inhibition of HIV protease," Bioorg. Med. Chem., 1994, 2(10), 1085–90.

Hauske, James R. et al., "Investigation of the effects of synthetic, non–cytotoxic immunophilin inhibitors on MDR," Bioorg. Med. Chem. Lett., 1994, 4(17), 2097–102.

Mashkovskii, M.D. et al., 1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties, Khim.–Farm. Zh., 1993, 27(10), 16–20.

Ranganathan, Darshan et al., "Protein Backbone Modification by Novel Cα–C Side–Chain Scission," 1994, J. Am. Chem. Soc., 116(15), 6545–57.

Soai, Kenso and Ishizaki, Miyuki, "Asymmetric Synthesis of Functionalized tertiary alcohols by diastereoselective allylation of chiral –keto amides derived from (S)–proline esters: control of sterochemistry based on saturated coordination of Lewis acid," J. Org. Chem., 1986, 57(17) 3290–5. (English).

Soai, Kenso et al., "Asymmetric synthesis of both enantiomers of –hydroxy acids by the diastereoselective reduction of chiral –keto amides with complex metal hydrides in the presence of a metal salt," Chem. Lett., 1986, 11, 1897–900.

Soai, Kenso and Hasegawa, Hitoshi, "Diastereoselective reduction of chiral –ketoamides derived from (S)–proline esters with sodium borohydride. Preparation of optically active –hydroxy acids," J. Chem. Soc., 1985, 1(4), 769–72.

Soai, Kenso and Ishizaki, Miyuki, "Diastereoselective asymmetric allylation of chiral –keto amides with allyltrimethylsilane. Preparation of protected homoallylic alcohols," J. Chem. Soc., 1984, 15, 1016–17.

Soai, Kenso et al., "Sodium borohydride as diastereoselective reducing agent of chiral –keto amides," Pept. Chem., 1982, 20, 81–4.

Bender, D., et al., "Periodate oxidation of –keto γ–lactams. Enol oxidation and β–lactam formation. Mechanism of periodate hydroxlation reactions," J. Org. Chem., 1978, 43(17), 3354–62.

Colombo, L. et al., "Enantioselective synthesis of secondary alcohols in the presence fo chiral ligands," Tetrahedron, 1982, 38(17), 2725–7.

Soai, Kenso et al., "Unusual effect of mixed solvent on the asymmetric reduction of chiral α–keto amides with sodium borohydride," J. Chem. Soc., 1982, 21, 1282–3.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Cushman, D.W. et al., "Design of potent competitive inhibitors of angiotensin–converting enzyme. Caboxylalkanoyl and mercaptoalkanoyl amino acids," Biochemistry, 1977, 16(25), 5484–91.

Steglich, Wolfgang and Hinze, Sabine, "A rational synthesis of N–triluoroacetylamino acids," Synthesis, 1976, 8, 399–401. (German).

Bycroft, Barrie W., and Lee, Grahame R., "Efficient asymmetric synthesis of .alpha.–amino from .alpha.–keto acids and ammonia with conservation of the chiral reagent," J. Chem. Soc., 1975, 24, 988–9.

Askin, D. et al., "Efficient Degradation of FK–506 to a versatile synthetic intermediate," J. Org. Chem., 1990, 55(20), 5451–4.

Goulet, Mark T., and Boger, Joshua, "Degradative studies on the tricarbonyl containing macrolide rapamycin," Tetrahedron Lett., 1990, 31(34), 4845–8.

Jones, T. et al., "Chemistryof tricarbonyl hemiketals and application of Evans technology to the total synthesis of the immunosuppresant (–)–FK–506," J. Am. Chem. Soc., 1990, 112(8), 2998–3017.

Jones, A. et al., "A formal synthesis of FK–506. Exploration of some alternatives to macrolactamization,"J. Org. Chem., 1990, 55(9), 2786–97.

Rao, A.V., et al., "Studies directed towards the synthesis of immunosuppresive agent FK–506: construction of the tricarbonyl moiety," Tetrahedron Lett., 1990, 31(10), 1439–42.

Harding, M.W., et al., "A receptor for the immunosuppresive FK506 is a cis–trans peptidyl–prolyl isomerase," Nature Lett., 1989, 341, 758–60.

Finberg, Robert W. et al., "Prevention of HIV–1 Infection and Preservation of CD4 Function by the Binding of CPFs to gp120," Science, 1990, 249, 287–91.

Goodfellow, Val S. et al., "p–Nitrophenyl 3–diazopyruvate and diazopyruvamide, a New Family of Photoactivatable Cross–Linking Bioprobes," Biochemistry, 28(15), 6346–60.

Wasserman, H.H. et al., "Synthesis of the tricarbonyl region of FK–506 through an amidophosphorane [Erratum to document cited in CA111(7):57366p]," J. Org. Chem., 1989, 54(22), 5406.

Wasserman, H.H. et al., "Synthesis of the tricarbonyl region of FK–506 through an amidosphere," J. Org. Chem., 1989, 54(12), 2785–6.

Dragovich et al., "Structured–Based Design of Novel, Urea–Containing FKBP12 Inhibitors," J. Med. Chem., 1996, 39, 1872–1884.

Gold et al., The Immunosuppressant FK506 Increases the Rate of Axonal Regeneration in Rat Sciatic Nerve, The Journal of Neuroscience, 1995, 15(11), 7509–7516.

Gold et al, "The Immunosuppressant FK506 increases functional recovery and nerve regeneration following peripheral nerve injury," Restorative Neurology and Neuroscience, 1994, 6, 287–296.

Lyons et al., "Immunosuppressant FK506 promotes neurite outgrowth in culture of PC12 cells and sensory ganglia," Proc. Natl. Acad. Sci. USA, 1994, 91, 3191–3195.

Gold, et al, "Multiple signals underlie the anatomy–induced up–regulation of c–JUN in adult sensory neurons," Neuroscience Letters 176, 1994, 123–127.

Gold et al., "Regulation of the transcription factor c–JUN by nerve growth factor in adult sensory neurons," Neuroscience Letters 154, 1993, 129–133.

Askin, D. et al., "Chemistry of FK–506: benzilic acid rearrangement of the tricarbonyl system," Tetrahedron Lett., 1989, 30(6), 671–4.

Coleman, R., and Danishefsky, S., "Degradation and manipulations of the immunosupressant FK506: preparation of potantial synthetic intemediates," Heterocycles, 1989, 28(1), 157–61.

Faelth, Lars et al., "Interactions between C=S groups in 1,2 and 1,3–bis(thiocarbonyl) Compounds: A Study by Spectroscopy, X–Ray Crystallography, and CNDO/S Calculations," Theochem, 1989, 55, 239–59.

Doulmedais, Ali et al., "Sterochemistry of Electrochemical Reduction of Optically Active –ketoamides. II. Electrorduction of benzoylformamides derived from S–(–)–proline," Bull. Soc. Chim. Fr., 1989, (2), 185–01. (French).

Soai, Kenso et al., "Asymmetric Allylation of –keto amides Derived from (S)–proline esters," Pept. Chem., 1986, 24, 327–30.

Munegumi, M. et al., "Asymmetric Catalytic Hydrogenations of N–pyruvoyl–(s)–proline esters," Bull. Chem. Soc. Jpn., 1987, 60(1), 243–53.

GPI Neuroimmunophilin Ligands Protect Striatal
Tyrosine Hydroxylase Levels from MPTP-Toxicity in Mice

HETEROCYCLIC THIOESTERS AND KETONES This application is a continuation-in-part of U.S. patent application Ser. No. 08/721,765, filed Sep. 25, 1996, the entire content of which is herein incorporated by reference.

BACKGROUND OF THE INVENTION

1. Field of Invention

This invention relates to neurotrophic low molecular weight, small molecule heterocyclic thioesters and ketones having an affinity for FKBP-type immunophilins, and their use as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science,* 1990, vol. 250, pp. 556–559. Instead, immunosuppression appears to stem from the formulation of a complex of immunosuppressant drug and immunophilin. It has been shown that the immunophilin-drug complexes interact with ternary protein targets as their mode of action. Schreiber et al., *Cell,* 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

It has been found that picomolar concentrations of an immunosuppressant such as FK506 and rapamycin stimulate neurite outgrowth in PC12 cells and sensory neurons, namely dorsal root ganglion cells (DRGs). Lyons et al., *Proc. of Natl. Acad. Sci.,* 1994, vol. 91, pp. 3191–3195. In whole animal experiments, FK506 has been shown to stimulate nerve regeneration following facial nerve injury.

Surprisingly, it has been found that certain compounds with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders, such as Alzheimer's disease, Parkinson's disease and amyotrophic lateral sclerosis (ALS), may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.,* 1991, 1:162); neurological deficits, such as involuntary tremors, or non-specific cerebral angina, such as non-localized headaches (De Groen et al., *N. Engl. J. Med.,* 1987, 317:861); and vascular hypertension with complications resulting therefrom (Kahan et al., *N. Engl. J. Med.,* 1989, 321:1725).

To prevent the side effects associated with use of the immunosuppressant compounds, the present invention provides non-immunosuppressive compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease) and amyotrophic lateral sclerosis.

SUMMARY OF THE INVENTION

The present invention relates to neurotrophic low molecular weight, small molecule compounds having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the compounds of the present invention is that they do not exert any significant immunosuppressive activity in addition to their neurotrophic activity.

Specifically, the present invention relates to a compound of formula II:

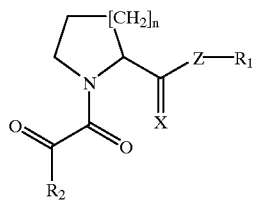

or a pharmaceutically acceptable salt thereof, wherein:

n is 1 or 2;

X is O or S;

Z is selected from the group consisting of S, $CH_2$, $CHR_1$ and $C(R_1)_2$;

$R_1$ is selected from the group consisting of $C_1$–$C_5$ straight or branched chain alkyl, $C_2$–$C_5$ straight or branched chain alkenyl, $Ar_1$ and mixtures thereof, wherein said $R_1$ is unsubstituted or substituted with halo, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, $Ar_1$ or a mixture thereof;

$R_2$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and $Ar_1$; and $Ar_1$ is phenyl, benzyl, pyridyl, fluorenyl, thioindolyl or naphthyl wherein said $Ar_1$ is unsubstituted or substituted with halo, hydroxy, nitro, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino or a mixture thereof.

The present invention also relates to a pharmaceutical composition comprising:

(i) an effective amount of the compound of formula II for effecting a neuronal activity; and (ii) a pharmaceutically acceptable carrier.

The present invention further relates to a method of effecting a neuronal activity in an animal, comprising:

administering to the animal an effective amount of the compound of formula II.

DETAILED DESCRIPTION OF THE INVENTION

Definitions

Figure 1:
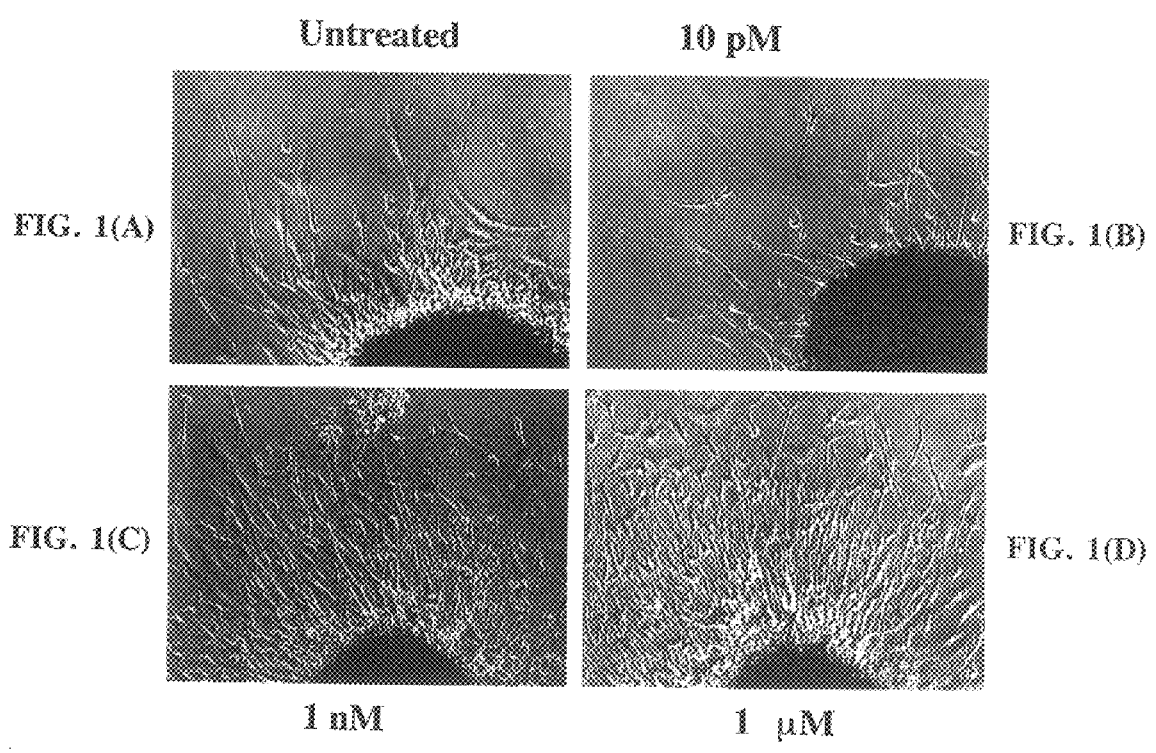
FIG. 1(A) is a representative photomicrograph of untreated sensory neurons.
FIG. 1(B) is a representative photomicrograph of compound 1 (10 pM) promoting neurite outgrowth in sensory neurons.
FIG. 1(C) is a representative photomicrograph of compound 1 (1 nM) promoting neurite outgrowth in sensory neurons.
FIG. 1(D) is a representative photomicrograph of compound 1 (1 μM) promoting neurite outgrowth in sensory neurons.
Figure 2:
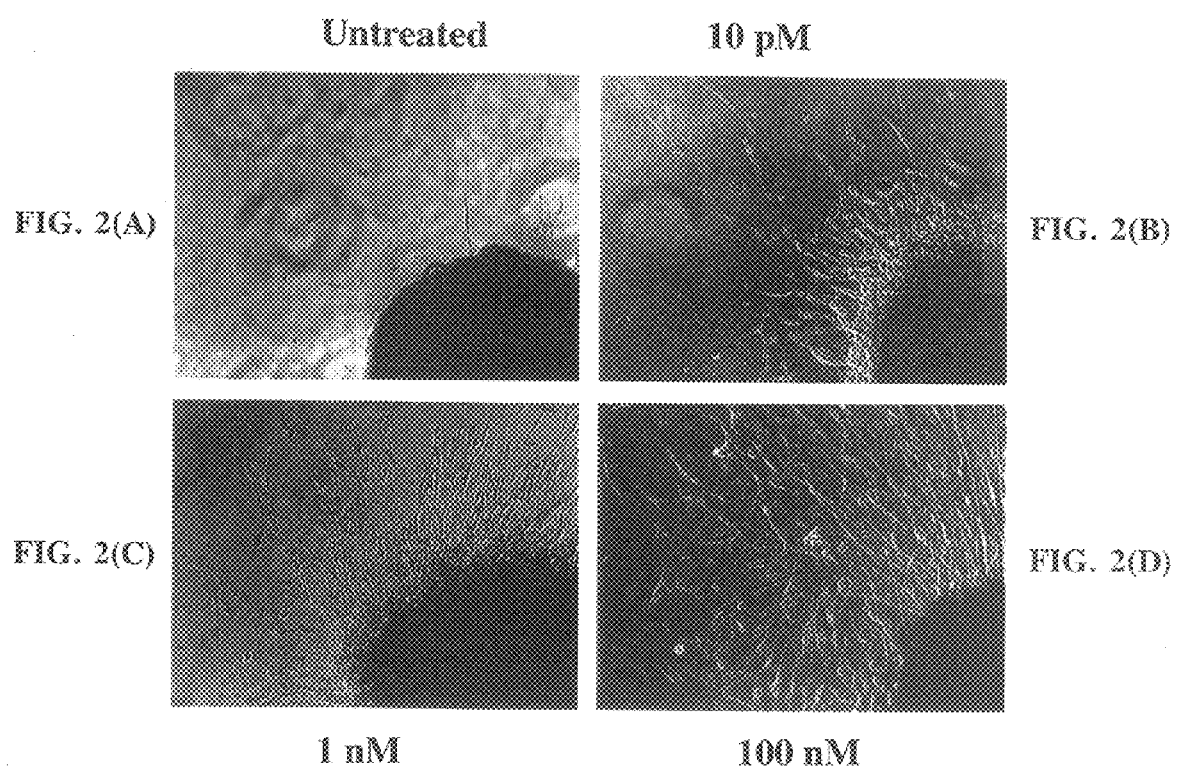
FIG. 2(A) is a representative photomicrograph of untreated sensory neurons.
FIG. 2(B) is a representative photomicrograph of compound 9 (10 pM) promoting neurite outgrowth in sensory neurons.
FIG. 2(C) is a representative photomicrograph of compound 9 (1 nM) promoting neurite outgrowth in sensory neurons.
FIG. 2(D) is a representative photomicrograph of compound 9 (100 nM) promoting neurite outgrowth in sensory neurons.
Figure 3:
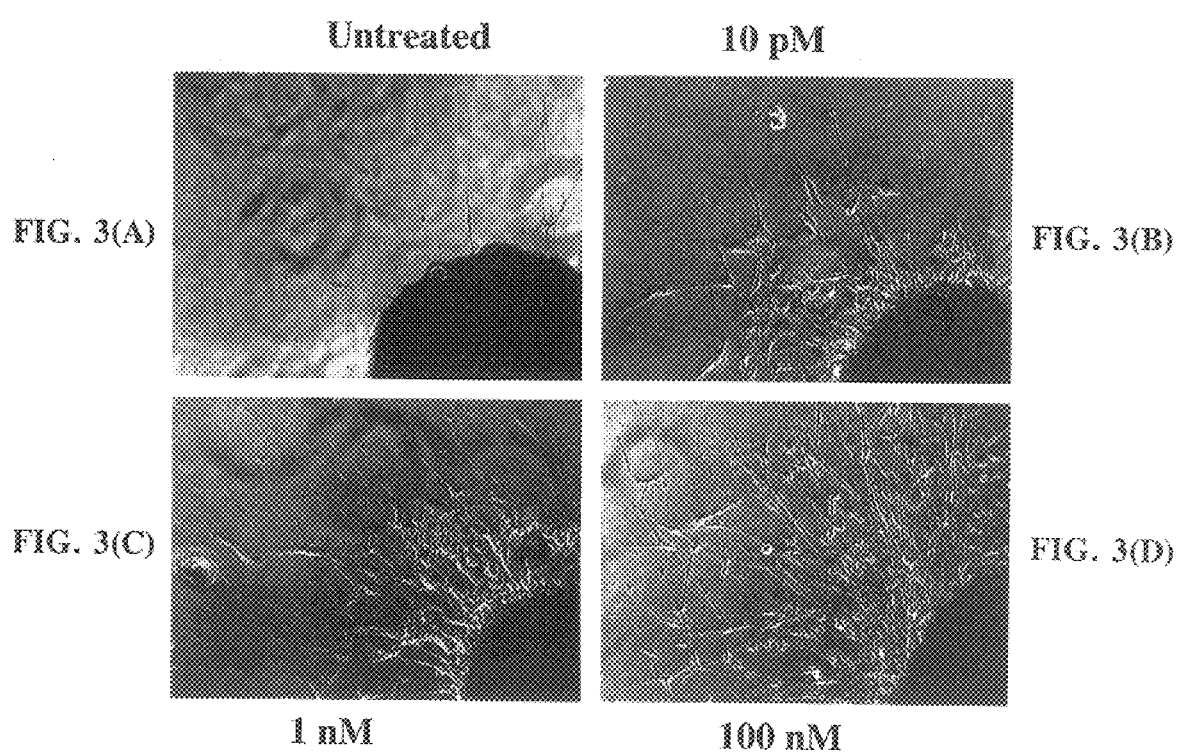
FIG. 3(A) is a representative photomicrograph of untreated sensory neurons.
FIG. 3(B) is a representative photomicrograph of compound 10 (10 pM) promoting neurite outgrowth in sensory neurons.
FIG. 3(C) is a representative photomicrograph of compound 9 (1 nM) promoting neurite outgrowth in sensory neurons.
FIG. 3(D) is a representative photomicrograph of compound 9 (100 nM) promoting neurite outgrowth in sensory neurons.

"Alkyl" refers to a branched or unbranched saturated hydrocarbon chain containing 1 to 6 carbon atoms, such as methyl, ethyl, propyl, iso-propyl, butyl, iso-butyl, tert-butyl, n-pentyl, n-hexyl and the like, unless otherwise indicated.

"Alkoxy" refers to the group —OR wherein R is alkyl as herein defined. Preferably, R is a branched or unbranched saturated hydrocarbon chain containing 1 to 3 carbon atoms.

"Halo" refers to fluoro, chloro, bromo or iodo, unless otherwise indicated.

"Isomers" are different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Also, the basic nitrogen-containing groups can be quarternized with agents including: lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Phenyl" refers to any possible isomeric phenyl radical, optionally monosubstituted or multisubstituted with substituents selected from the group consisting of alkyl, alkoxy, hydroxy, halo and haloalkyl.

"Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

Compounds of the Invention

The neurotrophic low molecular weight, small molecule FKBP inhibitor compounds of this invention have an affinity for FKBP-type immunophilins, such as FKBP12. When the neurotrophic compounds of this invention are bound to an FKBP-type immunophilin, they have been found to inhibit the prolyl-peptidyl cis-trans isomerase activity, or rotamase, activity of the binding protein and unexpectedly stimulate neurite growth.

FORMULA I

In particular, this invention relates to a compound of formula I:

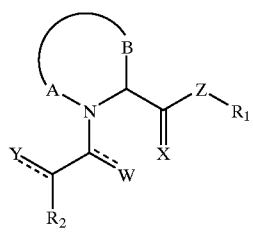

I or a pharmaceutically acceptable salt thereof, wherein:

A and B, together with the nitrogen and carbon atoms to which they are respectfully attached, form a 5–7 membered saturated or unsaturated heterocyclic ring containing any combination of $CH_2$, O, S, SO, $SO_2$, NH or $NR_2$ in any chemically stable oxidation state;

X is either O or S;

Z is either S, $CH_2$, $CHR_1$ or $C(R_1)_2$;

W and Y are independently O, S, $CH_2$ or $H_2$;

$R_1$ is $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$ or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino or a combination thereof; wherein the individual ring sizes are 5–6 members; and wherein the heterocyclic ring contains 1–6 heteroatom(s) selected from the group consisting of O, N, S and a combination thereof.

Suitable mono- and bicyclic, carbo- and heterocyclic rings include, without limitation, naphthyl, indolyl, furyl, thiazolyl, thienyl, pyridyl, quinolinyl, isoquinolinyl, fluorenyl and phenyl.

FORMULA II

A preferred embodiment of this invention is a compound of formula II:

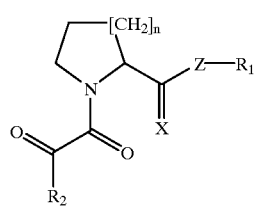

II or a pharmaceutically acceptable salt thereof, wherein:

n is 1 or 2;

X is O or S;

Z is selected from the group consisting of S, $CH_2$, $CHR_1$ and $C(R_1)_2$;

$R_1$ is selected from the group consisting of $C_1$–$C_5$ straight or branched chain alkyl, $C_2$–$C_5$ straight or branched chain alkenyl, $Ar_1$ and mixtures thereof, wherein said $R_1$ is unsubstituted or substituted with halo, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, $Ar_1$ or a mixture thereof;

$R_2$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and $Ar_1$; and $Ar_1$ is phenyl, benzyl, pyridyl, fluorenyl, thioindolyl or naphthyl wherein said $Ar_1$ is unsubstituted or substituted with halo, trifluoromethyl hydroxy, nitro, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino or a mixture thereof.

Specific examples of these embodiments are presented in TABLE I.

TABLE I

| No. | n | X | Z | R₁ | R₂ |
|---|---|---|---|---|---|
| 1 | 1 | O | CH₂ | 3-Phenylpropyl | 1,1-Dimethylpropyl |
| 2 | 1 | O | CH₂ | 3-(3-Pyridyl)propyl | 1,1-Dimethylpropyl |
| 3 | 1 | O | CH₂ | 3-Phenylpropyl | tert-Butyl |
| 4 | 1 | O | CH₂ | 3-(3-Pyridyl)propyl | tert-Butyl |
| 5 | 1 | O | CH₂ | 3-(3-Pyridyl)propyl | Cyclohexyl |
| 6 | 1 | O | CH₂ | 3-(3-Pyridyl)propyl | Cyclopentyl |
| 7 | 1 | O | CH₂ | 3-(3-Pyridyl)propyl | Cycloheptyl |
| 8 | 1 | O | CH₂ | 2-(9-Fluorenyl)ethyl | 1,1-Dimethylpropyl |
| 9 | 1 | O | S | 2-Phenethyl | 1,1-Dimethylpropyl |
| 10 | 2 | O | S | 2-Phenethyl | 1,1-Dimethylpropyl |
| 11 | 1 | O | S | Methyl(2-thioindole) | 1,1-Dimethylpropyl |
| 12 | 1 | O | S | 2-Phenethyl | Cyclohexyl |
| 13 | 2 | O | S | 2-Phenethyl | tert-Butyl |
| 14 | 2 | O | S | 2-Phenethyl | Phenyl |
| 15 | 1 | O | CH₂ | 3-(4-Methoxyphenyl)propyl | 1,1-Dimethylpropyl |
| 16 | 2 | O | CH₂ | 4-(4-Methoxyphenyl)butyl | 1,1-Dimethylpropyl |
| 17 | 2 | O | CH₂ | 4-Phenylbutyl | 1,1-Dimethylpropyl |
| 18 | 2 | O | CH₂ | 4-Phenylbutyl | Phenyl |
| 19 | 2 | O | CH₂ | 4-Phenylbutyl | Cyclohexyl |
| 20 | 1 | S | CH₂ | 3-Phenylpropyl | 1,1-Dimethylpropyl |
| 21 | 1 | S | S | 2-Phenethyl | 1,1-Dimethylpropyl |
| 22 | 2 | S | CH₂ | 3-Phenylpropyl | 1,1-Dimethylpropyl |
| 23 | 2 | S | S | 2-Phenethyl | 1,1-Dimethylpropyl |
| 24 | 2 | O | CHR₁ | 3-Phenylpropyl | 1,1-Dimethylpropyl |
| 25 | 2 | O | CHR₁ | 3-Phenylpropyl | Cyclohexyl |
| 26 | 2 | O | CHR₁ | 3-Phenylpropyl | Phenyl |
| 27 | 2 | O | CHR₁ | 3-Phenylpropyl | 3,4,5-Trimethoxyphenyl |
| 28 | 1 | O | S | 2-Phenethyl | Cyclopentyl |
| 29 | 2 | O | S | 3-Phenylpropyl | tert-Butyl |
| 30 | 1 | O | S | 3-Phenylpropyl | 1,1-Dimethylpropyl |
| 31 | 1 | O | S | 3-(3-Pyridyl)propyl | 1,1-Dimethylpropyl |
| 32 | 1 | O | S | 3-Phenylpropyl | Cyclohexyl |
| 33 | 1 | O | S | 4-Phenylbutyl | Cyclohexyl |
| 34 | 1 | O | S | 4-Phenylbutyl | 1,1-Dimethylpropyl |
| 35 | 1 | O | S | 3-(3-Pyridyl)propyl | Cyclohexyl |
| 36 | 1 | O | S | 3,3-Diphenylpropyl | 1,1-Dimethylpropyl |
| 37 | 1 | O | S | 3,3-Diphenylpropyl | Cyclohexyl |
| 38 | 1 | O | S | 3-(4-Methoxyphenyl)propyl | 1,1-Dimethylpropyl |
| 39 | 2 | O | S | 4-Phenylbutyl | tert-Butyl |
| 40 | 2 | O | S | 1,5-Diphenyl-3-sentyl | 1,1-Dimethylpropyl |
| 41 | 2 | O | S | 1,5-Diphenyl-3-sentyl | Phenyl |
| 42 | 2 | O | S | 3-(4-Methoxyphenyl)propyl | 1,1-Dimethylpropyl |
| 43 | 2 | O | S | 3-(4-Methoxyphenyl)propyl | Phenyl |
| 44 | 2 | O | S | 3-(1-Naphthyl)propyl | 1,1-Dimethylpropyl |
| 45 | 1 | O | S | 3,3-Di(4-fluoro)phenyl-propyl | 1,1-Dimethylpropyl |
| 46 | 1 | O | S | 4,4-Di(4-fluoro)phenyl-butyl | 1,1-Dimethylpropyl |
| 47 | 1 | O | S | 3-(1-Naphthyl)propyl | 1,1-Dimethylpropyl |
| 48 | 1 | O | S | 2,2-Diphenylethyl | 1,1-Dimethylpropyl |
| 49 | 2 | O | S | 2,2-Diphenylethyl | 1,1-Dimethylpropyl |
| 50 | 2 | O | S | 3,3-Diphenylpropyl | 1,1-Dimethylpropyl |
| 51 | 1 | O | S | 3-(4-{Trifluoromethyl}-phenyl)propyl | 1,1-Dimethylpropyl |
| 52 | 1 | O | S | 3-(2-Naphthyl)propyl | 1,1-Dimethylpropyl |
| 53 | 2 | O | S | 3-(1-Naphthyl)propyl | 1,1-Dimethylpropyl |
| 54 | 1 | O | S | 3-(3-Chloro)phenylpropyl | 1,1-Dimethylpropyl |
| 55 | 1 | O | S | 3-(3-{Trifluoromethyl}-phenyl)propyl | 1,1-Dimethylpropyl |
| 56 | 1 | O | S | 3-(2-Biphenyl)propyl | 1,1-Dimethylpropyl |
| 57 | 1 | O | S | 3-(2-Fluorophenyl)propyl | 1,1-Dimethylpropyl |
| 58 | 1 | O | S | 3-(3-Fluorophenyl)propyl | 1,1-Dimethylpropyl |
| 59 | 2 | O | S | 4-Phenylbutyl | 1,1-Dimethylpropyl |
| 60 | 2 | O | S | 3-Phenylpropyl | 1,1-Dimethylpropyl |
| 61 | 1 | O | S | 3-(2-Chloro)phenylpropyl | 1,1-Dimethylpropyl |
| 62 | 2 | O | S | 3-(3-Chloro)phenylpropyl | 1,1-Dimethylpropyl |
| 63 | 2 | O | S | 3-(2-Fluoro)phenylpropyl | 1,1-Dimethylpropyl |
| 64 | 2 | O | S | 3-(3-Fluoro)phenylpropyl | 1,1-Dimethylpropyl |
| 65 | 1 | O | S | 3-(3,4-Dimethoxyphenyl)propyl | 1,1-Dimethylpropyl |
| 66 | 1 | O | CH₂ | 3-Phenylpropyl | Cyclohexyl |
| 67 | 1 | O | CH₂ | 3-Phenylethyl | tert-Butyl |
| 68 | 2 | O | CH₂ | 4-Phenylbutyl | Cyclohexyl |
| 69 | 2 | O | CHR₁ | 2-Phenylethyl | tert-Butyl |
| 70 | 1 | O | CH₂ | 3,3-Di(4-fluorophenyl)-propyl | 1,1-Dimethylpropyl |
| 71 | 2 | O | CH₂ | 3-Phenylpropyl | 1,1-Dimethylpropyl |

The most preferred examples of TABLE I are named as follows:

(2S)-3,3-dimethyl-1-[2-(5phenylpentanoyl)pyrrolidinyl]pentane-1,2-dione (2S)-3,3-dimethyl-1-[2-(5-(3-pyridyl)pyrrolidinyl]pentane-1,2-dione
(2S)-2-(1-Oxo-5-phenyl)pentyl-1(3,3-dimethyl-1,2-dioxobutyl)pyrrolidine
2-Phenyl-1-ethyl (2S)-1-(3,3-dimethyl-1,2-dioxopentyl)-2-pyrrolidinecarbothioate
2-Phenyl-1-ethyl 1-(3,3-dimethyl-1,2-dioxopentyl)-2-piperidinecarbothioate
1-{2-[(benzo[b]thiophen-3-ylmethylthio)carbonyl]pyrrolidinyl}-3,3-dimethylpentane-1,2-dione
2-Phenyl-1-ethyl (2S)-1-(2-cyclohexyl-1,2-dioxoethyl)-2-pyrrolidinecarbothioate
2-Phenyl-1-ethyl 1-(2-phenyl-1,2-dioxoethyl)-2-piperidinecarbothioate
2-Phenyl-1-ethyl (2S)-1-(2cyclopentyl-1,2-dioxoethyl)-2-pyrrolidinecarbothioate
3-Phenyl-1-propyl 1-(3,3-dimethyl-1,2-dioxobutyl)-2-piperidinecarbothioate
3-Phenyl-1-propyl (2S)-1-(3,3-dimethyl-1,2-dioxopentyl)-2-pyrrolidinecarbothioate
3-(3-Pyridyl)-1-propyl (2S)-1-(3,3-dimethyl-1,2-dioxopentyl)-2-pyrrolidinecarbothioate
3-Phenyl-1-propyl (2S)-1-(2-cyclohexyl-1,2-dioxoethyl)-2-pyrrolidinecarbothioate
4-Phenyl-1-butyl (2S)-1-(2-cyclohexyl-1,2-dioxoethyl)-2-pyrrolidinecarbothioate
4-Phenyl-1-butyl (2S)-1-(3,3-dimethyl-1,2-dioxopentyl)-2-pyrrolidinecarbothioate
3-(3-Pyridyl)-1-propyl (2S)-1-(2-cyclohexyl-1,2-dioxoethyl)-2-pyrrolidinecarbothioate
3,3-Diphenyl-1-propyl (2S)-1-(3,3-dimethyl-1,2-dioxopentyl)-2-pyrrolidinecarbothioate
3,3-Diphenyl-1-propyl (2S)-1-(2-cyclohexyl-1,2-dioxopentyl)-2-pyrrolidinecarbothioate
3-(para-Methoxyphenyl)-1-propyl (2S)-1-(3,3-dimethyl-1,2-dioxopentyl)-2-pyrrolidinecarbothioate
4-Phenyl-1-butyl 1-(1,2-dioxo-3,3-dimethylbutyl)-2-piperidinecarbothioate
1,5-Diphenyl-3-pentyl 1-(3,3-dimethyl-1,2-dioxopentyl)-2-piperidinecarbothioate
1,5-Diphenyl-3-pentyl 1-(2-phenyl-1,2-dioxoethyl)-2-piperidinecarbothioate
3-(para-Methoxyphenyl)-1-propyl 1-(1,2-dioxo-3,3-dimethylpentyl)piperidine-2-carbothioate
3-(para-Methoxyphenyl)-1-propyl 1-(2-phenyl-1,2-dioxoethyl)piperidine-2-carbothioate
3-(1-Naphthyl)-1-propyl 1-(3,3-dimethyl-1,2-dioxopentyl)piperidine-2-carbothioate
3,3-Di(para-fluoro)phenyl-1-propyl (2S)-1-(3,3-dimethyl-1,2-dioxopentyl)-2-pyrrolidinecarbothioate
4,4-Di(para-fluorophenyl)butyl 1-(3,3-dimethyl-2-oxopentanoyl)-2-pyrrolidinecarbothioate
3-(1-Naphythyl)-1-propyl (2S)-1--(3,3-dimethyl-2-oxopentanoyl)-2-pyrrolidinecarbothioate
2,2-Diphenylethyl (2S)-1-(3,3-dimethyl-2-oxopentanoyl)-2-pyrroldinecarbothioate
2,2-Diphenylethyl (2S)-1-(3,3-dimethyl-2-oxopentanoyl)-2-piperidinecarbothioate
3,3-Diphenylpropyl (3,3-dimethyl-2-oxopentanoyl)-2-piperidinecarbothioate
3-[4-(Trifluoromethyl)phenyl]propyl (2S)-1-(3,3-dimethyl-2-oxopentanoyl)-2-pyrrolidinecarbothioate
3-(2-Naphthyl)propyl (2S)-1-(3,3-dimethyl-2-oxopentanoyl)-2-pyrrolidinecarbothioate
3-(1-Naphthyl)-1-propyl 1-(3,3-dimethyl-2-oxopentanoyl)-2-piperidinecarbothioate
3-(3–Chlorophenyl)propyl (2S)-1-(3,3-dimethyl-2-oxopentanoyl)-2-pyrrolidinecarbothioate
3-[3-(Trifluoromethyl)phenyl]propyl (2S)-1-(3,3-dimethyl-2oxopentanoyl)-2-pyrrolidinecarbothioate
3-(2-Biphenyl)propyl (2S)-1-(3,3-dimethyl-2-oxopentanoyl)-2-pyrrolidinecarbothioate
3-(2-Fluorophenyl)propyl (2S)-1-(3,3-dimethyl-2-oxopentanoyl)-2-pyrrolidinecarbothioate
3-(3-Fluorophenyl)propyl (2S)-1-(3,3-dimethyl-2-oxopentanoyl)-2-pyrrolidinecarbothioate
4-Phenylbutyl 1-(3,3-dimethyl-2-oxopentanoyl)-2-piperidinecarbothioate
60 3-Phenylpropyl 1-(3,3-dimethyl-2-oxopentanoyl)-2-piperidinecarbothioate
3-(2-Chlorophenyl)propyl (2S)-1-(3,3-dimethyl-2-oxopentanoyl)-2-pyrrolidinecarbothioate
3-(3-Chlorophenyl)-1-propyl 1-(3,3-dimethyl-2-oxopentanoyl)-2-piperidinecarbothioate
3-(2-Fluorophenyl)propyl 1-(3,3-dimethyl-2-oxopentanoyl)-2-piperidinecarbothioate
3-(3-Fluorophenyl)propyl 1-(3,3-dimethyl-2-oxopentanoyl)-2-piperidinecarbothioate
3-(3,4-Dimethoxyphenyl)propyl(2S)-1-(3,3-dimethyl-2-oxopentanoyl)-2-pyrrolidinecarbothioate
(2S)-2-(1-Oxo-5-phenyl)pentyl-1-(2-Cyclohexyl-1,2-dioxoethyl)pyrrolidine
2-(1-Oxo-4-phenyl)-butyl-1-(3,3-dimethyl-1,2-dioxobutyl)pyrrolidine
2-({1-Oxo-6-phenyl}-butyl-1-(3,3-dimethyl-1,2-dioxobutyl)pyrrolidine
(2S)-2-({1-Oxo-4-phenyl}-butyl-1-(2–Cyclohexyl-1,2-dioxoethyl)pyrrolidine
2-({1-Oxo-[2-{2'-phenyl}ethyl]-4-phenyl}-butyl-1-(3,3-dimethyl-1,2-dioxobutyl)piperidine
(2S)-2-[5,5-di(4-Fluorophenyl)pentanoyl]-1-(3,3-dimethyl-1,2-pentanedione)pyrrolidine
3,3-Dimethyl-1-[2-(5-phenylpentanoyl)piperidino]-1,2-pentanedione

FORMULA III

Another preferred embodiment is a compound of formula III:

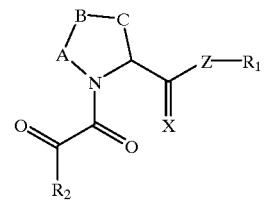

or a pharmaceutically acceptable salt thereof, wherein:

A, B, C and D are independently $CH_2O$, S, SO, $SO_2$, NH or $NR_2$;

X is O or S;

Z is S, $CH_2$, $CHR_1$ or $C(R_1)_2$;

$R_1$ is $C_1$–$C_6$ straight or branched chain alkyl or alkenyl, which is substituted in one or more position(s) with $(Ar_1)$ n $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$ or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino or a combination thereof; wherein the individual ring sizes are 5–6 members; and wherein the heterocyclic ring contains 1–6 heteroatom(s) selected from the group consisting of O, N, S and a combination thereof.

Particularly preferred compounds of formula III are presented in TABLE II.

TABLE II

| No. | A | B | C | X | Z | $R_1$ | $R_2$ |
|---|---|---|---|---|---|---|---|
| 72 | $CH_2$ | S | $CH_2$ | O | S | 2-phenethyl | 3,3-dimethylpentyl |
| 73 | $CH_2$ | S | $CH_2$ | O | $CH_2$ | 3-phenylpropyl | 3,3-dimethylpentyl |
| 74 | $CH_2$ | $CH_2$ | NH | O | S | 2-phenethyl | 3,3-dimethylpentyl |
| 75 | $CH_2$ | S | $CH_2$ | S | S | 2-phenethyl | 3,3-dimethylpentyl |

FORMULA IV

A further preferred embodiment of this invention is a compound of formula IV:

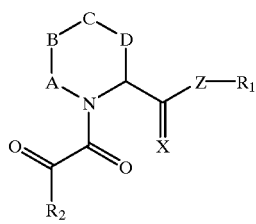

IV or a pharmaceutically acceptable salt thereof, wherein:

A, B, C and D are independently $CH_2$, O, S, SO, $SO_2$, NH or $NR_2$;

X is O or S;

Z is S, $CH_2$, $CHR_1$ or $C(R_1)_2$;

$R_1$ is $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$ or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino or a combination thereof; wherein the individual ring sizes are 5–6 members; and wherein the heterocyclic ring contains 1–6 heteroatom(s) selected from the group consisting of O, N, S and a combination thereof.

Particularly preferred compounds of formula IV are presented in TABLE III.

TABLE III

| No. | A | B | C | D | X | Z | $R_1$ | $R_2$ |
|---|---|---|---|---|---|---|---|---|
| 76 | $CH_2$ | $CH_2$ | O | $CH_2$ | O | $CH_2$ | 3-phenylpropyl | 3,3-dimethylpentyl |
| 77 | $CH_2$ | $CH_2$ | O | $CH_2$ | O | S | 2-phenethyl | 3,3-dimethylpentyl |
| 78 | $CH_2$ | $CH_2$ | S | $CH_2$ | O | $CH_2$ | 3-phenylpropyl | 3,3-dimethylpentyl |
| 79 | $CH_2$ | $CH_2$ | S | $CH_2$ | O | S | 2-phenethyl | 3,3-dimethylpentyl |

The compounds of this invention possess asymmetric centers and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis, or by resolving the compound of formula (I). It is understood that the individual stereoisomers as well as mixtures (racemic and non-racemic) of stereoisomers are encompassed by the scope of the present invention. The compounds of this invention possess at least one asymmetric center and thus can be produced as mixtures of stereoisomers or as individual R- and S-stereoisomers. The individual enantiomers may be obtained by resolving a racemic or non-racemic mixture of an intermediate at some appropriate stage of the synthesis. It is understood that the individual R- and S- stereoisomers as well as mixtures of stereoisomers are encompassed by this invention. The S-stereoisomer is most preferred due to its greater activity.

Methods of Using the Compounds of the Invention

The compounds of the present invention have an affinity for the FK506 binding protein, particularly FKBP12, which is present in the brain. When the inventive compounds bind to FKBP in the brain, they exhibit excellent neurotrophic activity. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention further relates to a method of effecting a neuronal activity in an animal, comprising:

administering to the animal a neurotrophically effective amount of a compound of formula I, II, III or IV.

In a preferred embodiment, the neuronal activity is selected from the group consisting of stimulation of damaged neurons, promotion of neuronal regeneration, prevention of neurodegeneration and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria or Guillain-Barre syndrome; Alzheimer's disease; and Parkinson's disease.

The compounds of the present invention are particularly useful for treating a neurological disorder selected from the group consisting of: peripheral neuropathy caused by physical injury or disease state, traumatic injury to the brain, physical damage to the spinal cord, stroke associated with brain damage, and neurological disorder relating to neurodegeneration. Examples of neurological disorders relating to neurodegeneration are Alzheimer's Disease, Parkinson's Disease and amyotrophic lateral sclerosis.

For these purposes, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the compounds should readily penetrate the blood-brain barrier when peripherally administered. Compounds which cannot penetrate the blood-brain barrier can be effectively administered by an intraventricular route.

The compounds may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

Furthermore, the compounds may be administered topically, especially when the conditions addressed for treatment involve areas or organs readily accessible by topical application, including neurological disorders of the eye, the skin or the lower intestinal tract. Suitable topical formulations can be readily prepared for each of these areas.

For topical application to the eye, or ophthalmic use, the compounds can be formulated as micronized suspensions in isotonic, pH adjusted sterile saline, or, preferably, as a solution in isotonic, pH adjusted sterile saline, either with or without a preservative such as benzylalkonium chloride. Alternatively, the compounds may be formulated into ointments, such as petrolatum, for ophthalmic use.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in a rectal suppository formulations (see above) or in suitable enema formulations.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disease being treated; and the form of administration.

The compounds can be administered with other neurotrophic agents such as neurotrophic growth factor (NGF), glial derived growth factor, brain derived growth factor, ciliary neurotrophic factor and neurotropin-3. The dosage level of other neurotrophic drugs will depend upon the factors previously stated and the neurotrophic effectiveness of the drug combination.

Pharmaceutical Compositions of the Invention

The present invention also relates to a pharmaceutical composition comprising:

(i) a neurotrophically effective amount of the compound of formula I, II, III or IV, and (ii) a pharmaceutically acceptable carrier.

The above discussion relating to the utility and administration of the compounds of the present invention also applies to the pharmaceutical compositions of the present invention.

EXAMPLES

The following examples are illustrative of the present invention and are not intended to be limitations thereon. Unless otherwise specified, all percentages are based on 100% by weight of the final compound.

Example 1

Synthesis of (2S)-2-(1-oxo-5-phenyl-1-pentyl-1-(3, 3-dimethyl-1,2-dioxopentyl)pyrrolidine (1)

(2S)-2-(l-oxo-4-phenyl)butyl-N-benzylpyrrolidine 1-chloro-4-phenylbutane (1.78 g; 10.5 mmol) in 20 mL of THF was added to 0.24 g (10 mmol) of magnesium turnings in 50 mL of refluxing THF. After the addition was complete, the mixture was refluxed for an additional 5 hours, and then added slowly to a refluxing solution of N-benzyl-L-proline ethyl ester (2.30 g (10 mmol) in 100 mL of THF. After 2 hours of further reflux, the mixture was cooled and treated with 5 mL of 2 N HCl. The reaction mixture was diluted with ether (100 mL) and washed with saturated $NaHCO_3$, water and brine. The organic phase was dried, concentrated and chromatographed, eluting with 5:1 $CH_2Cl_2$:EtOAc to obtain 2.05 g (64%) of the ketone as an oil, $^1H$ NMR ($CDCl_3$; 300 MHz): 1.49–2.18 (m, 8H); 2.32–2.46 (m, 1H); 2.56–2.65 (m, 2H); 2.97–3.06 (m, 1H); 3.17–3.34 (m, 1H); 3.44–3.62 (m, 1H); 4.02–4.23 (m, 2H); 7.01–7.44 (m, 10H).

(2S)-2-(1-oxo-4-phenyl) butylpyrrolidine

The ketone compound (500 mg) and palladium hydroxide (20% on carbon, 50 mg) was hydrogenated at 40 psi in a Paar shaker overnight. The catalyst was removed by filtration and the solvent was removed in vacuo. The free amine was obtained as a yellow oil (230 mg; 100%), $^1H$ NMR ($CDCl_3$; 300 MHz): 1.75–2.34 (m, 1OH); 2.55 (m, 2H); 2.95 (dm, 1H); 3.45–3.95 (m, 1H); 4.05 (m, 1H); 7.37 (m, 5H).

(2S)-2-(1-oxo-4-phenyl)butyl-1-(1,2-dioxo-2-methoxyethyl)pyrrolidine

To a solution of (2S)-2-(1-oxo-4-phenyl)butylpyrrolidine (230 mg; 1.0 mmol) in $CH_2C_{12}$(20 mL) at 0° C. was added dropwise methyloxalyl chloride (135 mg; 1.1 mmol). After stirring at 0° C. for 3 hours, the reaction was quenched with saturated $NH_4Cl$ and the organic phase was washed with water and brine and dried and concentrated. The crude residue was purified on a silica gel column, eluting with 20:1 $CH_2Cl_2$:EtOAc to obtain 300 mg of the oxamate as a clear oil (98%), $^1H$ NMR ($CDCl_3$; 300 MHz): 1.68 (m, 4H); 1.91–2.38 (m, 4H); 2.64 (t, 2H); 3.66–3.80 (m, 2H); 3.77, 3.85 (s, 3H total); 4.16 (m, 2H); 4.90 (m, 1H); 7.16 (m, 3H); 7.27 (m, 2H).

(2S)-2-({1-oxo-5-ohenyl}-pentyl-1-(3,3-dimethyl-1, 2-dioxopentyl)pyrrolidine (1)

To a solution of the oxamate above (250 mg; 0.79 mmol) in anhydrous ether (15 mL), cooled to −78° C., was added 1,1-dimethylpropyl-magnesium chloride (0.8 mL of a 1.0 M solution in ether; 0.8 mmol) . After stirring the resulting mixture at −78° C. for 2 hours, the reaction was quenched by the addition of 2 mL of saturated $NH_4Cl$, followed by 100 mL of EtOAc. The organic phase was washed with brine, dried, concentrated, and purified on a silica gel column, eluting with 50:1 $CH_2Cl_2$:EtOAc. Compound 1 was obtained as a clear oil, 120 mg, $^1H$ NMR ($CDCl_3$, 300 MHz): δ0.87 (t, 3H, J=7.5); 1.22 (s, 3H); 1.25 (s, 3H); 1.67 (m, 4H); 1.70–2.33 (m, 6H); 2.61 (t, 2H, J=7.1); 3.52 (m, 2H) 4.17 (t, 2H, J=6.2); 4.52 (m, 1H); 7.16–7.49 (m, 5H) Anal. Calcd. for $C_{22}H_{31}NO_3$—$H_2O$: C, 70.37; H, 8.86; N, 3.73. Found: 70.48; H, 8.35; N, 3.69.

Example 2

Synthesis of 2-phenyl-1-ethyl 1-(3,3-dimethyl-1,2-dioxopentyl)-2-piperidinecarbothioate (10)

Methyl(2S)-1-(1,2-dioxo-2-methoxyethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 mL) was added dropwise. The resulting mixture was stirred at 0° C. for 1.5 hour. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1H$ NMR ($CDCl_3$): δ 1.93 (dm, 2H); 2.17(m, 2H); 3.62(m, 2H); 3.71 (s, 3H); 3.79, 3.84 (s, 3H total); 4.86 (dd, 1H, J=8.4, 3.3).

Methyl (2S)-1-(1 2-dioxo-3, 3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil, $^1$H NMR (CDCl$_3$): δ 0.88 (t, 3H); 1.22, 1.26 (s, 3H each); 1.75(dm, 2H); 1.87–2.10 (m, 3H); 2.23 (m, 1H); 3.54 (m, 2H); 3.76 (s, 3H); 4.52 (dm, 1H, J=8.4, 3.4).

(2S)-1-(1,2-dioxo-3,3-dimethylpentyl)-2-pyrrolidine-carboxylic acid

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 minutes and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification, $^1$H NMR (CDCl$_3$): δ 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

2-phenyl-1-ethyl1-(3,3-dimethyl-1,2-dioxopentyl)-2-piperidinecarbothioate (9)

To a solution of (2S)-1-(1,2-dioxo-3,3-dimethylpentyl)-2-pyrrolidinecarboxylic acid (241 mg; 1.0 mmol) in CH$_2$C$_{12}$ (10 mL) was added dicyclohexylcarbodiimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of CH$_2$C$_{12}$. The mixture was allowed to warm to room temperature with stirring overnight. The solids were removed by filtration and the filtrate was concentrated in vacuo; the crude residue was purified by flash chromatography (10:1 hexane:EtOAc) to obtain 302 mg (84%) of 9 as an oil, $^1$H NMR (CDCl$_3$, 300 MHz): δ 0.85 (t, 3H, j=7.5) 1.29 (s, 3H); 1.31 (s, 3H); 1.70–2.32 (m, 6H); 2.92 (t, 2H, j=7.4); 3.22(t, 2H, J=7.4); 3.58 (m, 2H); 4.72 (m, 1H); 7.23–7.34 (m, 5H). Anal. Calcd. for C$_{20}$H$_{27}$NO$_3$S —0.4H$_2$0: C, 65.15; H, 7.60; N, 3.80. Found: C, 65.41; H, 7.49; N, 3.72.

Example 3

Synthesis of 2-phenyl-1-ethyl (2S)-1-(3,3-dimethyl-1,2-dioxopentyl)-2-pyrrolidinecarbothioate (9)

Methyl 1-(1,2-dioxo-2-methoxyethyl)-2-piperidine-carboxylate

A solution of methyl pipecolate hydrochloride (8.50 g; 47.31 mmol) in dry methylene chloride (100 mL) was cooled to 0° C. and treated with triethylamine (10.5 g; 103 mmol; 2.1 eq) . After stirring the formed slurry under a nitrogen atmosphere for 15 minutes, a solution of methyl oxalyl chloride (8.50 g; 69.4 mmol) in methylene chloride (75 mL) was added dropwise. The resulting mixture was stirred at 0° C. for 1.5 hours. After filtering to remove solids, the organic phase was washed with water, dried over MgSO$_4$ and concentrated. The crude residue was purified on a silica gel column, eluting with 50% ethyl acetate in hexane, to obtain 9.34 g (86%) of the product as a reddish oil. Mixture of cis-trans amide rotamers; data for trans rotamer given. $^1$H NMR (CDCl$_3$): δ 1.22–1.45 (m, 2H); 1.67–1.78 (m, 3H); 2.29 (m, 1H); 3.33 (m, 1H); 3.55 (m, 1H); 3.76 (s, 3H); 3.85, 3.87 (s, 3H total); 4.52 (dd, 1H).

Methyl 1-(1,2-dioxo-3,3-dimethylpentyl)-2-piperidine-carboxylate

A solution of methyl 1-(1,2-dioxo-2-methoxyethyl)-2-piperidinecarboxylate (3.80 g; 16.57 mmol) in 75 mL of tetrahydrofuran (THF) was cooled to −78° C. and treated with 20.7 mL of a 1.0 M solution of 1,1-dimethyl-propylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 3.32 g (74%) of the oxamate as a colorless oil, $^1$H NMR (CDCl$_3$) δ 0.88 (t, 3H); 1.21, 1.25 (s, 3H each); 1.35–1.80 (m, 7H); 2.35 (m, 1H); 3.24 (m, 1H); 3.41 (m, 1H); 3.76 (s, 3H); 5.32 (d, 1H).

1-(1,2-dioxo-3,3-dimethylpentyl)-2-piperidine-carboxylic acid

A mixture of methyl 1-(1,2-dioxo-3,3-dimethylpentyl)-2-piperidinecarboxylate (3.30 g; 12.25 mmol), 1 N LiOH (15 mL), and methanol (60 mL) was stirred at 0° C. for 30 minutes and at room temperature overnight. The mixture was acidified to pH 1 with 1 N HCl, diluted with water, and extracted into 100 mL of methylene chloride. The organic extract was washed with brine and concentrated to deliver 2.80 g (87%) of snow-white solid which did not require further purification, $^1$H NMR (CDCl$_3$): δ 0.89 (t, 3H); 1.21, 1.24 (s, 3H each); 1.42–1.85 (m, 7H); 2.35 (m, 1H); 3.22 (d, 1H); 3.42(m, 1H); 5.31 (d, 1H).

2-phenyl-1-ethyl (2S)-1-(3,3-dimethyl-1,2-dioxopentyl)-2-pyrrolidinecarbothioate (10)

To a solution of 1-(1,2-dioxo-3,3-dimethylpentyl)-2-piperidine-carboxylic acid (255 mg; 1.0 mmol) in CH$_2$C$_{12}$ (10 mL) was added dicyclohexylcarbodiimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of CH$_2$C$_{12}$. The mixture was allowed to warm to room temperature with stirring overnight. The solids were removed by filtration and the filtrate was concentrated in vacuo; the crude residue was purified by flash chromatography (10:1 hexane:EtOAc) to obtain 300 mg (80%) of 10 as an oil, $^1$H NMR (CDCl$_3$, 300 MHz): δ 0.94 (t, 3H, J=7.5); 1.27 (s, 3H); 1.30 (s, 3H); 1.34–1.88 (m, 7H); 2.45 (m, 1H); 2.90 (t, 2H, J=7.7); 3.26 (t, 2H, J=7.7); 3.27 (m, 1H); 3.38 (m, 1H); 5.34 (m, 1H); 7.24–7.36 (m, 5H) Anal. Calcd. for C$_{21}$H$_{29}$NO$_3$S: C, 67.17; H, 7.78; N, 3.73. Found: C, 67.02; H, 7.83; N, 3.78.

As discussed above, the compounds of the present invention have an affinity for the FK506 binding protein, particularly FKBP12. The inhibition of the prolyl peptidyl cis-trans isomerase activity of FKBP may be measured as an indicator of this affinity.

K$_i$ Test Procedure

Inhibition of the peptidyl-prolyl isomerase (rotamase) activity of the inventive compounds can be evaluated by known methods described in the literature (Harding et al., *Nature*, 1989, 341:758–760; Holt et al. *J. Am. Chem. Soc.*, 115:9923–9938). These values are obtained as apparent K$_i$'s and are presented for representative compounds in Table IV. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table IV under the column "$K_i$".

The neurotrophic effects of the compounds of the present invention can be demonstrated in cellular biological experiments in vitro, as described below.

Chick Dorsal Root Ganglion

Cultures and Neurite Outgrowth

The neurotrophic effects of the FKBP inhibitor compounds were demonstrated by evaluating the ability of the compounds to promote neurite outgrowth in cultured chick sensory neurons from dorsal root ganglia. Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

Dose-response curves were generated from which $ED_{50}$ values were obtained. The results of these experiments are presented in Table IV under the column "ED50". Representative photomicrographs of untreated (control) sensory neurons and of compounds 1 (10 pM, 1 nM, 1 $\mu$M), 9 (10 pM, 1 nM, 100 nM) and 10 (10 pM, 1 nM, 100 nM) promoting neurite outgrowth in sensory neurons are shown in FIG.'s 1(A–D), 2(A–D) and 3(A–D), respectively.

MPTP Model of Parkinson's Disease

The remarkable neurotrophic and neuroregenerative effects of the present inventive compounds were further demonstrated in an animal model of neurodegenerative disease. MPTP lesioning of dopaminergic neurons in mice was used as an animal model of Parkinson's Disease. Four week old male CD1 white mice were dosed i.p. with 30 mg/kg of MPTP for 5 days. Test compounds (4 mg/kg), or vehicle, were administered s.c. along with the MPTP for 5 days, as well as for an additional 5 days following cessation of MPTP treatment. At 18 days following MPTP treatment, the animals were sacrificed and the striata were dissected and homogenized. Immunostaining was performed on saggital and coronal brain sections using anti-tyrosine hydroxylase 1 g to quantitate survival and recovery of dopaminergic neurons. In animals treated with MPTP and vehicle, a substantial loss of functional dopaminergic terminals was observed as compared to non-lesioned animals. Lesioned animals receiving test compounds showed a significant recovery of TH-stained dopaminergic neurons.

Figure 4:
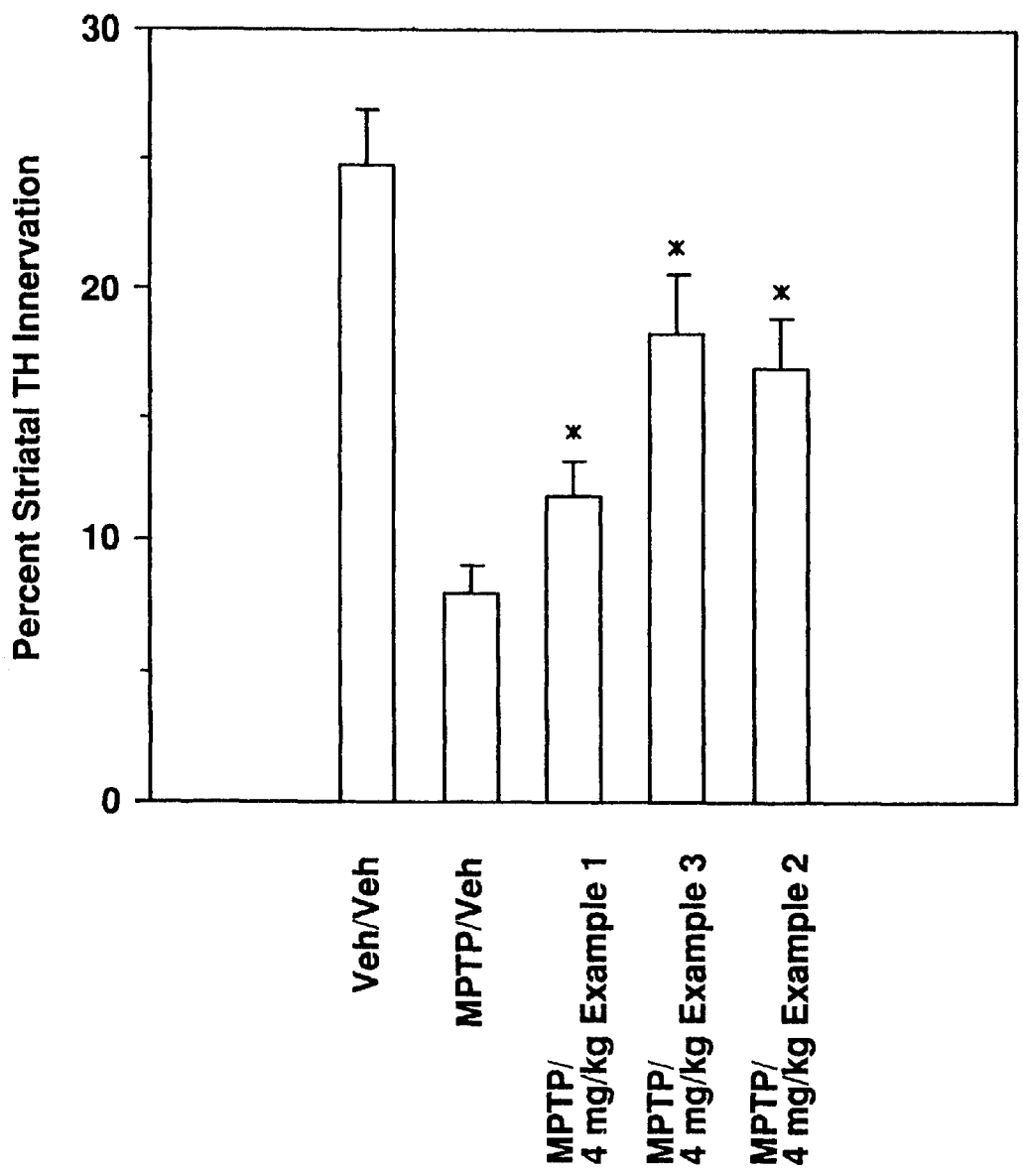
FIG. 4 presents quantitation for the recovery of TH-positive dopaminergic neurons in the striatum of animals receiving compounds 1, 9 and 10.

The results of these experiments are presented in TABLE IV under the column "% TH recovery". Quantitation for the recovery of TH-positive dopaminergic neurons in the striatum of animals receiving compounds 1, 9 and 10, and for representative control and lesioned animals not receiving the test drugs, are presented in FIG. 4.

TABLE IV

| | In Vitro Test Results | | |
|---|---|---|---|
| Example # | Ki, nM | ED50, nM | % TH recovery |
| 1 | 31 | 0.4 | 23 |
| 2 | 210 | — | — |
| 3 | 85 | — | — |
| 9 | 104 | 0.5 | 61 |
| 10 | 12 | 0.8 | 54 |
| 11 | 299 | 0.36 | 53 |
| 12 | 442 | 0.025 | — |
| 14 | 313 | 0.9 | 48 |
| 28 | 108 | 0.9 | 41 |
| 29 | 59 | 0.003 | 50 |
| 30 | 11 | 0.00025 | 65 |
| 31 | 8.7 | — | 31 |
| 32 | 362 | — | 52 |
| 33 | 1698 | — | — |
| 34 | 34 | 0.9 | 48 |
| 35 | 62 | — | — |
| 36 | 7 | — | 56 |
| 37 | 68 | — | — |
| 38 | 8.9 | 0.011 | 37.32 |
| 39 | 347 | — | — |
| 40 | 1226 | | |
| 41 | 366 | — | — |
| 42 | 28 | — | — |
| 43 | 259 | — | — |
| 44 | 188 | — | 25 |
| 45 | 31 | — | — |
| 46 | 757 | — | — |
| 47 | 21 | — | 50 |
| 48 | 127 | — | 28 |
| 49 | 1334 | — | — |
| 50 | 55 | — | 62 |
| 51 | 33 | — | — |
| 52 | 6 | — | — |
| 53 | 261 | — | — |
| 54 | 37 | — | — |
| 55 | 30 | — | — |
| 56 | 880 | — | — |
| 57 | 57 | — | — |
| 58 | 79 | — | — |
| 59 | 962 | — | — |
| 60 | 90 | — | — |
| 61 | 139 | — | — |
| 62 | 196 | — | — |
| 63 | 82 | — | — |
| 64 | 163 | — | — |
| 65 | 68 | — | — |
| 66 | 306 | 5 | 38 |
| 67 | 177 | — | — |
| 68 | 284 | — | — |
| 69 | 49 | — | 23 |
| 70 | 457 | — | 25 |
| 71 | 788 | — | — |

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

We claim:
1. A compound of formula II:

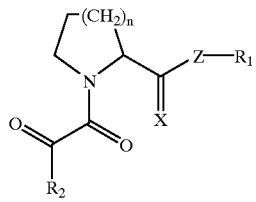

or a pharmaceutically acceptable salt thereof, wherein:
n is 1 or 2;
X is O or S;
Z is S;
$R_1$ is selected from the group consisting of $C_1$–$C_5$ straight or branched chain alkyl, $C_2$–$C_5$ straight or branched chain alkenyl, $Ar_1$ and mixtures thereof, wherein said $R_1$ is unsubstituted or substituted with halo, nitro, $C_1$–$C_6$ straight or branched chain alkyl, $C_2$–$C_6$ straight or branched chain alkenyl, hydroxy, $C_1$–$C_4$ alkoxy, $C_2$–$C_4$ alkenyloxy, phenoxy, benzyloxy, amino, $Ar_1$ or a mixture thereof;
$R_2$ is selected from the group consisting of $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and $Ar_1$, provided that $R_2$ is not methyl when n is 1, X is O, and $R_1$ is phenyl;
$Ar_1$ is phenyl, benzyl, pyridyl, fluorenyl, thioindolyl or naphthyl wherein said $Ar_1$ is unsubstituted or substituted with halo, trifluoromethyl, hydroxy, nitro, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino or a mixture thereof.

2. The compound of claim 1, wherein:
n is 1; and
X is O.

3. The compound of claim 2, wherein Z is S.

4. The compound of claim 3, which is selected from the group consisting of:
2-Phenyl-1-ethyl (2S)-1-(3,3-dimethyl-1,2-dioxopentyl)-2-pyrrolidinecarbothioate;
1-{2-[(benzo[b]thiophen-3-ylmethylthio)carbonyl] pyrrolidinyl}-3,3-dimethylpentane-1,2-dione;
2-Phenyl-1-ethyl (2S)-1-(2-cyclohexyl-1 2-dioxoethyl)-2-pyrrolidinecarbothioate;
2-Phenyl-1-ethyl (2S)-1-(2-cyclopentyl-1,2-dioxoethyl)-2-pyrrolidinecarbothioate;
3-Phenyl-1-propyl (2S)-1-(3,3-dimethyl-1,2-dioxopentyl)-2-pyrrolidinecarbothioate;
3-(3-Pyridyl)-1-propyl(2S)-1-(3,3-dimethyl-1,2-dioxopentyl)-2-pyrrolidinecarbothioate;
3-Phenyl-1-propyl (2S)-1-(2-cyclohexyl-1,2-dioxoethyl)-2-pyrrolidinecarbothioate;
4-Phenyl-1-butyl (2S)-1-(2-cyclohexyl-1,2-dioxoethyl)-2-pyrrolidinecarbothioate;
4-Phenyl-1-butyl (2S)-1-(3,3-dimethyl-1,2-dioxopentyl)-2-pyrrolidinecarbothioate;
3-(3-Pyridyl)-1-propyl (2S)-1-(2-cyclohexyl-1,2-dioxoethyl)-2-pyrrolidinecarbothioate;
3,3-Diphenyl-1-propyl (2S)-1-(3,3-dimethyl-1,2-dioxopentyl)-2-pyrrolidinecarbothioate;
3,3-Diphenyl-1-propyl (2S)-1-(2-Cyclohexyl-1,2-dioxoethyl)-2-pyrrolidinecarbothioate;
3-(para-Methoxyphenyl)-1-propyl (2S)-1-(3,3-dimethyl-1,2-dioxopentyl)- 2 -pyrrolidinecarbothioate;
3,3-Di(para-Fluoro)phenyl-1-propyl (2S)-1-(3,3-dimethyl-1,2-dioxopentyl)- 2 -pyrrolidinecarbothioate;
4,4-Di(para-fluorophenyl)butyl 1-(3,3-dimethyl-2-oxopentanoyl)-2-pyrrolidinecarbothioate;
3-(1-Naphthyl)-1-propyl (2S)-1-(3,3-dimethyl - 2 -oxopentanoyl)- 2 -pyrrolidinecarbothioate;
2,2-Diphenylethyl (2S)-1-(3,3-dimethyl-2-oxopentanoyl)-2-pyrrolidinecarbothioate;
3-[4-(Trifluoromethyl)phenyl]propyl (2S)-1-(3,3-dimethyl-2-oxopentanoyl)-2-pyrrolidinecarbothioate;
3-(2-Naphthyl)propyl (2S)-1-(3,3-dimethyl-2-oxopentanoyl)-2-pyrrolidinecarbothioate;
3-(3–Chlorophenyl)propyl (2S)-1-(3,3-dimethyl-2-oxopentanoyl)-2-pyrrolidinecarbothioate;
3-[3-(Trifluoromethyl)phenyl]propyl (2S)-1-(3,3-dimethyl-2-oxopentanoyl)-2-pyrrolidinecarbothioate;
3-(2-Biphenyl)propyl (2S)-1-(3,3-dimethyl-2-oxopentanoyl)-2-pyrrolidinecarbothioate;
3-(2-Fluorophenyl)propyl (2S)-1-(3,3-dimethyl-2-oxopentanoyl)-2-pyrrolidinecarbothioate;
3-(3-Fluorophenyl)propyl (2S)-1-(3,3-dimethyl-2-oxopentanoyl)-2-pyrrolidinecarbothioate;
3-(2–Chlorophenyl)propyl (2S)-1-(3,3-dimethyl-2-oxopentanoyl)-2-pyrrolidinecarbothioate; and
3-(3,4-Dimethoxyphenyl)propyl (2S)-1-(3,3-dimethyl-2-oxopentanoyl)-2-pyrrolidinecarbothioate.

5. The compound of claim 1, wherein:
n is 1; and
X is S.

6. The compound of 5, wherein Z is S.

7. The compound of claim 1, wherein:
n is 2; and
X is O.

8. The compound of claim 7, wherein Z is S.

9. The compound of claim 8, which is selected from the group consisting of:
2-Phenyl-1-ethyl 1-(3,3-dimethyl-1,2-dioxopentyl)-2-piperidinecarbothioate;
2-Phenyl-1-ethyl 1-(2-phenyl-1,2-dioxoethyl)-2-piperidinecarbothioate;
3-Phenyl-1-propyl 1-(3,3-dimethyl-1,2-dioxobutyl)-2-piperidinecarbothioate;
4-Phenyl-1-butyl 1-(1,2-dioxo-3,3-dimethylbutyl)-2-piperidinecarbothioate;
1,5-Diphenyl-3-pentyl 1-(3,3-dimethyl-1,2-dioxopentyl)-2-piperidinecarbothioate;
1,5-Diphenyl-3-pentyl 1-(2-phenyl-1,2-dioxoethyl)-2-piperidinecarbothioate;
3-(para-Methoxyphenyl)-1-propyl 1-(1,2-dioxo-3,3-dimethylpentyl)piperidine-2-carbothioate;
3-(para-Methoxyphenyl)-1-propyl 1-(2-phenyl-1,2-dioxoethyl)piperidine-2-carbothioate;
3-(1-Naphthyl)-1-propyl 1-(3,3-dimethyl-1,2-dioxopentyl)piperidine-2-carbothioate;

2,2-Diphenylethyl (2S)-1-(3,3-dimethyl-2-oxopentanoyl)-2-piperidinecarbothioate;

3,3-Diphenylpropyl 1-(3,3-dimethyl-2-oxopentanoyl)-2-piperidinecarbothioate;

3-(1-Naphthyl)-1-propyl 1-(3,3-dimethyl-2-oxopentanoyl)-2-piperidinecarbothioate;

4-Phenylbutyl 1-(3,3-dimethyl-2-oxopentanoyl)-2-piperidinecarbothioate;

3-Phenylpropyl 1-(3,3-dimethyl-2-oxopentanoyl)-2-piperidinecarbothioate;

3-(3–Chlorophenyl)-1-propyl 1-(3.3-dimethyl-2-oxopentanoyl)-2-piperidinecarbothioate;

3-(2-Fluorophenyl)propyl 1-(3,3-dimethyl-2-oxopentanoyl)-2-piperidinecarbothioate; and 3-(3-Fluorophenyl)propyl 1-(3,3-dimethyl-2-oxopentanoyl)-2-piperidinecarbothioate.

10. The compound of claim 1, wherein:

n is 2; and

X is S.

11. The compound of claim 15, wherein Z is S.

12. A pharmaceutical composition comprising:

(i) an effective amount of the compound of claim 1 for effecting a neuronal activity; and (ii) a pharmaceutically acceptable carrier.

13. The pharmaceutical composition of claim 12, wherein, in said compound:

n is 1; and

X is O.

14. The pharmaceutical composition of claim 13, wherein, in said compound, Z is S.

15. The pharmaceutical composition of claim 14, wherein said compound is selected from the group consisting of:

2-Phenyl-1-ethyl (2S)-1-(3,3-dimethyl-1,2-dioxopentyl)-2-pyrrolidinecarbothioate;

1-{2-[(benzo[b]thiophen-3-ylmethylthio) carbonyl] pyrrolidinyl }-3,3-dimethylpentane-1,2-dione;

2-Phenyl-1-ethyl (2S)-1-(2-cyclohexyl-1,2-dioxoethyl)-2-pyrrolidinecarbothioate;

2-Phenyl-1-ethyl (2S)-1-(2-cyclopentyl-1,2-dioxoethyl)-2-pyrrolidinecarbothioate;

3-Phenyl-1-propyl (2S)-1-(3,3-dimethyl-1,2-dioxopentyl)-2-pyrrolidinecarbothioate;

3-(3-Pyridyl)-1-propyl(2S)-1-(3,3-dimethyl-1,2-dioxopentyl)-2-pyrrolidinecarbothioate;

3-Phenyl-1-propyl (2S)-1-(2-cyclohexyl-1,2-dioxoethyl)-2-pyrrolidinecarbothioate;

4-Phenyl-1-butyl (2S)-1-(2-cyclohexyl-1,2-dioxoethyl)-2-pyrrolidinecarbothioate;

4-Phenyl-1-butyl (2S)-1-(3,3-dimethyl-1,2-dioxopentyl)-2-pyrrolidinecarbothioate;

3-(3-Pyridyl)-1-propyl (2S)-1-(2-cyclohexyl-1,2-dioxoethyl)-2-pyrrolidinecarbothioate;

3,3-Diphenyl-1-propyl (2S)-1-(3,3-dimethyl-1,2-dioxopentyl)-2-pyrrolidinecarbothioate;

3,3-Diphenyl-1-propyl (2S)-1-(2-Cyclohexyl-1,2-dioxoethyl)-2-pyrrolidinecarbothioate;

3-(para-Methoxyphenyl)-1-propyl (2S)-1-(3,3-dimethyl-1,2-dioxopentyl)-2-pyrrolidinecarbothioate;

3,3-Di(para-Fluoro)phenyl-1-propyl (2S)-1-(3,3-dimethyl-1,2-dioxopentyl)-2-pyrrolidinecarbothioate;

4,4-Di(para-fluorophenyl)butyl 1-(3,3-dimethyl-2-oxopentanoyl)-2-pyrrolidinecarbothioate;

3-(1-Naphthyl)-1-propyl (2S)-1-(3,3-dimethyl-2-oxopentanoyl)-2-pyrrolidinecarbothioate;

2,2-Diphenylethyl (2S)-1-(3,3-dimethyl-2-oxopentanoyl)-2-pyrrolidinecarbothioate;

3-[4-(Trifluoromethyl)phenyl]propyl (2S)-1-(3,3-dimethyl-2-oxopentanoyl)-2-pyrrolidinecarbothioate;

3-(2-Naphthyl)propyl (2S)-1-(3,3-dimethyl-2-oxopentanoyl)-2-pyrrolidinecarbothioate;

3-(3-Chlorophenyl)propyl (2S)-1-(3,3-dimethyl-2-oxopentanoyl)-2-pyrrolidinecarbothioate;

3-[3-(Trifluoromethyl)phenyl]propyl (2S)-1-(3,3-dimethyl-2-oxopentanoyl)-2-pyrrolidinecarbothioate;

3-(2-Biphenyl)propyl (2S)-1-(3,3-dimethyl-2-oxopentanoyl)-2-pyrrolidinecarbothioate;

3-(2-Fluorophenyl)propyl (2S)-1-(3,3-dimethyl-2-oxopentanoyl)-2-pyrrolidinecarbothioate;

3-(3-Fluorophenyl)propyl (2S)-1-(3,3-dimethyl-2-oxopentanoyl)-2-pyrrolidinecarbothioate;

3-(2–Chlorophenyl)propyl (2S)-1-(3,3-dimethyl-2-oxopentanoyl)-2-pyrrolidinecarbothioate; and 3-(3,4-Dimethoxyphenyl)propyl (2S)-1-(3,3-dimethyl-2-oxopentanoyl)-2-pyrrolidinecarbothioate.

16. The pharmaceutical composition of claim 12, wherein, in said compound:

n is 1; and

X is S.

17. The pharmaceutical composition of 16, wherein, in said compound, Z is S.

18. The pharmaceutical composition of claim 12, wherein, in said compound:

n is 2; and X is O.

19. The pharmaceutical composition of claim 18, wherein, in said compound, Z is S.

20. The pharmaceutical composition of claim 19, wherein said compound is selected from the group consisting of:

2-Phenyl-1-ethyl 1-(3,3-dimethyl-1,2-dioxopentyl)-2-piperidinecarbothioate;

2-Phenyl-1-ethyl 1-(2-phenyl-1,2-dioxoethyl)-2-piperidinecarbothioate;

3-Phenyl-1-propyl 1-(3,3-dimethyl-1,2-dioxobutyl)-2-piperidinecarbothioate;

4-Phenyl-1-butyl 1-(1,2-dioxo-3,3-dimethylbutyl)-2-piperidinecarbothioate;

1,5-Diphenyl-3-pentyl 1-(3,3-dimethyl-1,2-dioxopentyl)-2-piperidinecarbothioate;

1,5-Diphenyl-3-pentyl 1-(2-phenyl-1.2-dioxoethyl)-2-piperidinecarbothioate;

3-(para-Methoxyphenyl)-1-propyl 1-(1,2-dioxo-3,3-dimethylpentyl)piperidine-2-carbothioate;

3-(para-Methoxyphenyl)-1-propyl 1-(2-phenyl-1,2-dioxoethyl)piperidine-2-carbothioate;

3-(1-Naphthyl)-1-propyl 1-(3,3-dimethyl-1,2-dioxopentyl)piperidine-2-carbothioate;

2,2-Diphenylethyl (2S)-1-(3,3-dimethyl-2-oxopentanoyl)-2-piperidinecarbothioate;

3,3-Diphenylpropyl 1-(3,3-dimethyl-2-oxopentanoyl)-2-piperidinecarbothioate;

3-(1-Naphthyl)-1-propyl 1-(3,3-dimethyl-2-oxopentanoyl)-2-piperidinecarbothioate;

4-Phenylbutyl 1-(3,3-dimethyl-2-oxopentanoyl)-2-piperidinecarbothioate;

3-Phenylpropyl 1-(3,3-dimethyl-2-oxopentanoyl)-2-piperidinecarbothioate;

3-(3–Chlorophenyl)-1-propyl 1-(3,3-dimethyl-2-oxopentanoyl)-2-piperidinecarbothioate;

3-(2-Fluorophenyl)propyl 1-(3,3-dimethyl-2-oxopentanoyl)-2-piperidinecarbothioate; and 3-(3-Fluorophenyl)propyl 1-(3,3-dimethyl-2-oxopentanoyl)-2-piperidinecarbothioate.

21. The pharmaceutical composition of claim 12, wherein, in said compound:

n is 2; and

X is S.

22. The pharmaceutical composition of 21, wherein, in said compound, Z is S.

23. A method for effecting a neuronal activity in an animal, comprising:

administering to the animal an effective amount of the compound of claim 1.

24. The method of claim 23, wherein the neuronal activity is selected from the group consisting of stimulation of damaged neurons, promotion of neuronal regeneration, prevention of neurodegeneration and treatment of Parkinson's Disease.

25. The method of claim 23, wherein, in said compound:

n is 1; and

X is O.

26. The method of claim 25, wherein, in said compound, Z is S.

27. The method of claim 26, wherein said compound is selected from the group consisting of:

2-Phenyl-1-ethyl (2S)-1-(3,3-dimethyl-1,2-dioxopentyl)-2-pyrrolidinecarbothioate;

1-{2-[(benzo[b]thiophen-3-ylmethylthio) carbonyl] pyrrolidinyl}-3,3-dimethylpentane-1, 2-dione;

2-Phenyl-1-ethyl (2S)-1-(2-cyclohexyl-1,2-dioxoethyl)-2-pyrrolidinecarbothioate;

2-Phenyl-1-ethyl (2S)-1-(2-cyclopentyl-1,2-dioxoethyl)-2-pyrrolidinecarbothioate;

3-Phenyl-1-propyl (2S)-1-(3,3-dimethyl-1,2-dioxopentyl)-2-pyrrolidinecarbothioate;

3-(3-Pyridyl)-1-propyl(2S)-1-(3,3-dimethyl-1,2-dioxopentyl)-2-pyrrolidinecarbothioate;

3-Phenyl-1-propyl (2S)-1-(2-cyclohexyl-1,2-dioxoethyl)-2-pyrrolidinecarbothioate;

4-Phenyl-1-butyl (2S)-1-(2-cyclohexyl-1,2-dioxoethyl)-2-pyrrolidinecarbothioate;

4-Phenyl-1-butyl (2S)-1-(3,3-dimethyl-1,2-dioxopentyl)-2-pyrrolidinecarbothioate;

3-(3-Pyridyl)-1-propyl (2S)-1-(2-cyclohexyl-1.2-dioxoethyl)-2-pyrrolidinecarbothioate;

3,3-Diphenyl-1-propyl (2S)-1-(3,3-dimethyl-1,2-dioxopentyl)-2-pyrrolidinecarbothioate;

3,3-Diphenyl-1-propyl (2S)-1-(2-Cyclohexyl-1.2-dioxoethyl)-2-pyrrolidinecarbothioate;

3-(para-Methoxyphenyl)-1-propyl (2S)-1-(3,3-dimethyl-1,2-dioxopentyl)-2-pyrrolidinecarbothioate;

3,3-Di(para-Fluoro)phenyl-1-propyl (2S)-1-(3,3-dimethyl-1,2-dioxopentyl)-2-pyrrolidinecarbothioate;

4,4-Di(para-fluorophenyl)butyl 1-(3,3-dimethyl-2-oxopentanoyl)-2-pyrrolidinecarbothioate;

3-(1-Naphthyl)-1-propyl (2S)-1-(3,3-dimethyl-2-oxopentanoyl)-2-pyrrolidinecarbothioate;

2,2-Diphenylethyl (2S)-1-(3,3-dimethyl-2-oxopentanoyl)-2-pyrrolidinecarbothioate;

3-[4-(Trifluoromethyl)phenyl]propyl (2S)-1-(3,3-dimethyl-2-oxopentanoyl)-2-pyrrolidinecarbothioate;

3-(2-Naphthyl)propyl (2S)-1-(3,3-dimethyl-2-oxopentanoyl)-2-pyrrolidinecarbothioate;

3-(3-Chlorophenyl)propyl (2S)-1-(3,3-dimethyl-2-oxopentanoyl)-2-pyrrolidinecarbothioate;

3-(3-(Trifluoromethyl)phenyl) propyl (2S)-1-(3.3-dimethyl-2-oxopentanoyl)-2-pyrrolidinecarbothioate;

3-(2-Biphenyl)-propyl (2S)-1-(3,3-dimethyl-2-oxopentanoyl)-2-pyrrolidinecarbothioate;

3-(2-Fluorophenyl)propyl (2S)-1-(3,3-dimethyl-2-oxopentanoyl)-2-pyrrolidinecarbothioate;

3-(3-Fluorophenyl)propyl (2S)-1-(3,3-dimethyl-2-oxopentanoyl)-2-pyrrolidinecarbothioate;

3-(2–Chlorophenyl)propyl (2S)-1-(3,3-dimethyl-2-oxopentanoyl)-2-pyrrolidinecarbothioate; and 3-(3,4-Dimethoxyphenyl)propyl (2S)-1-(3,3-dimethyl-2-oxopentanoyl)-2-pyrrolidinecarbothioate.

28. The method of claim 23, wherein, in said compound:

n is 1; and

X is S.

29. The method of claim 28, wherein, in said compound, Z is S.

30. The method of claim 23, wherein, in said compound:

n is 2; and

X is O.

31. The method of claim 30, wherein, in said compound, Z is S.

32. The method of claim 31, wherein said compound is selected from the group consisting of:

2-Phenyl-1-ethyl 1-(3,3-dimethyl-1,2-dioxopentyl)-2-piperidinecarbothioate;

2-Phenyl-1-ethyl 1-(2-phenyl-1,2-dioxoethyl)-2-piperidinecarbothioate;

3-Phenyl-1-propyl 1-(3,3-dimethyl-1,2-dioxobutyl)-2-piperidinecarbothioate;

4-Phenyl-1-butyl 1-(1,2-dioxo-3,3-dimethylbutyl)-2-piperidinecarbothioate;

1,5-Diphenyl-3-pentyl 1-(3,3-dimethyl-1,2-dioxopentyl)-2-piperidinecarbothioate;

1,5-Diphenyl-3-pentyl 1-(2-phenyl-1,2-dioxoethyl)-2-piperidinecarbothioate;

3-(para-Methoxyphenyl)-1-propyl 1-(1,2-dioxo-3,3-dimethylpentyl)piperidine-2-carbothioate;

3-(para-Methoxyphenyl)-1-propyl 1-(2-phenyl-1,2-dioxoethyl)piperidine-2-carbothioate;

3-(1-Naphthyl)-1-propyl 1-(3,3-dimethyl-1,2-dioxopentyl)piperidine-2-carbothioate;

2,2-Diphenylethyl (2S)-1-(3,3-dimethyl-2-oxopentanoyl)-2-piperidinecarbothioate;

3,3-Diphenylpropyl 1-(3,3-dimethyl-2-oxopentanoyl)-2-piperidinecarbothioate;

3-(1-Naphthyl)-1-propyl 1-(3.3-dimethyl-2-oxopentanoyl)-2-piperidinecarbothioate;

4-Phenylbutyl 1-(3,3-dimethyl-2-oxopentanoyl)-2-piperidinecarbothioate;

3-Phenylpropyl 1-(3,3-dimethyl-2-oxopentanoyl)-2-piperidinecarbothioate;

3-(3–Chlorophenyl)-1-propyl 1-(3.3-dimethyl-2-oxopentanoyl)-2-piperidinecarbothioate;

3-(2-Fluorophenyl)propyl 1-(3,3-dimethyl-2-oxopentanoyl)-2-piperidinecarbothioate; and 3-(3-Fluorophenyl)propyl 1-(3,3-dimethyl-2-oxopentanoyl)-2-piperidinecarbothioate.

33. The method of claim 23, wherein, in said compound:
n is 2; and
X is S.

34. The method of 33, wherein, in said compound, Z is S.

35. A compound which is 3,3-Diphenyl-1-propyl (2S)-1-(3,3-dimethyl-1,2-dioxopentyl)-2-pyrrolidinecarbothioate.

36. A compound which is 3-(1-Naphthyl)-1-propyl (2S)-1-(3,3-dimethyl-2-oxopentanoyl)-2-pyrrolidinecarbothioate.

37. A compound which is 2,2-Diphenylethyl (2S)-1-(3,3-dimethyl-2-oxopentanoyl)-2-pyrrolidinecarbothioate.

38. A compound which is 3,3-Diphenylpropyl 1-(3,3-dimethyl-2-oxopentanoyl)-2-piperidinecarbothioate.

39. A compound which is 3- [4-(Trifluoromethyl)phenyl] propyl(2S)-1-(3,3-dimethyl-2-oxopentanoyl)-2-pyrrolidinecarbothioate.

40. A compound which is 3-(2-Naphthyl)propyl (2S)-1-(3,3-dimethyl-2-oxopentanoyl)-2-pyrrolidinecarbothioate.

41. The pharmaceutical composition of claim 12 which further comprises one or more neurotrophic agent(s).

42. The pharmaceutical composition of claim 41 wherein said one or more neurotrophic agent(s) is/are independently selected from the group consisting of neurotrophic growth factor (NGF), glial derived growth factor, brain derived growth factor, ciliary neurotrophic factor and neurotropin-3.

43. The pharmaceutical composition of claim 42, wherein said one or more neurotrophic agent(s) is neurotrophic growth factor (NGF).

44. A pharmaceutical composition comprising:
(i) an effective amount of 3,3-Diphenyl-1-propyl (2S)-1-(3,3-dimethyl-1,2-dioxopentyl)-2-pyrrolidinecarbothioate, or a pharmaceutically acceptable salt thereof, for effecting a neuronal activity; and
(ii) a pharmaceutically acceptable carrier.

45. A pharmaceutical composition comprising:
(i) an effective amount of 3-(1-Naphthyl)-1-propyl (2S)-1-(3,3-dimethyl-2-oxopentanoyl)-2-pyrrolidinecarbothioate, or a pharmaceutically acceptable salt thereof, for effecting a neuronal activity; and
(ii) a pharmaceutically acceptable carrier.

46. A pharmaceutical composition comprising:
(i) an effective amount of 2,2-Diphenylethyl (2S)-1-(3,3-dimethyl-2-oxopentanoyl)-2-pyrrolidinecarbothioate, or a pharmaceutically acceptable salt thereof, for effecting a neuronal activity; and
(ii) a pharmaceutically acceptable carrier.

47. A pharmaceutical composition comprising:
(i) an effective amount of 3,3-Diphenylpropyl 1-(3,3-dimethyl-2-oxopentanoyl)-2-piperidinecarbothioate, or a pharmaceutically acceptable salt thereof, for effecting a neuronal activity; and
(ii) a pharmaceutically acceptable carrier.

48. A pharmaceutical composition comprising:
(i) an effective amount of 3-(4-(Trifluoromethyl)phenyl)-propyl (2S)-1-(3,3-dimethyl-2-oxopentanoyl)-2-pyrrolidinecarbothioate, or a pharmaceutically acceptable salt thereof, for effecting a neuronal activity; and
(ii) a pharmaceutically acceptable carrier.

49. A pharmaceutical composition comprising:
(i) an effective amount of 3-(2-Naphthyl)propyl (2S)-1-(3,3-dimethyl-2-oxopentanoyl)-2-pyrrolidinecarbothioate, or a pharmaceutically acceptable salt thereof, for effecting a neuronal activity; and
(ii) a pharmaceutically acceptable carrier.

50. The method of claim 23, wherein said compound is administered in combination with one or more neurotrophic agent(s).

51. The method of claim 50, wherein said one or more neurotrophic agent(s) is/are independently selected from the group consisting of neurotrophic growth factor (NGF), glial derived growth factor, brain derived growth factor, ciliary neurotrophic factor and neurotropin-3.

52. The method of claim 51, wherein said one or more neurotrophic agent(s) is neurotrophic growth factor (NGF).

53. A method of effecting a neuronal activity in an animal, comprising:
administering to the animal an effective amount of 3,3-Diphenyl-1-propyl (2S)-1-(3,3-dimethyl-1,2-dioxopentyl)-2-pyrrolidinecarbothioate or a pharmaceutically acceptable salt thereof.

54. A method of effecting a neuronal activity in an animal, comprising:
administering to the animal an effective amount of 3-(1-Naphthyl)-1-propyl (2S)-1-(3,3-dimethyl-2-oxopentanoyl)-2-pyrrolidinecarbothioate or a pharmaceutically acceptable salt thereof.

55. A method of effecting a neuronal activity in an animal, comprising:
administering to the animal an effective amount of 2,2-Diphenylethyl (2S)-1-(3,3-dimethyl-2-oxopentanoyl)-2-pyrrolidinecarbothioate or a pharmaceutically acceptable salt thereof.

56. A method of effecting a neuronal activity in an animal, comprising:
administering to the animal an effective amount of 3,3-Diphenylpropyl 1-(3,3-dimethyl-2-oxopentanoyl)-2-piperidine-carbothioate or a pharmaceutically acceptable salt thereof.

57. A method of effecting a neuronal activity in an animal, comprising:
administering to the animal an effective amount of 3-[4-(Trifluoromethyl)phenyl]propyl (2S)-1-(3,3-dimethyl-2-oxopentanoyl)-2-pyrrolidinecarbothioate or a pharmaceutically acceptable salt thereof.

58. A method of effecting a neuronal activity in an animal, comprising:
administering to the animal an effective amount of 3-(2-Naphthyl)propyl (2S)-1-(3,3-dimethyl-2-oxopentanoyl)-2-pyrrolidinecarbothioate or a pharmaceutically acceptable salt thereof.

* * * * *

UNITED STATES PATENT AND TRADEMARK OFFICE
CERTIFICATE OF CORRECTION

PATENT NO. : 5,990,131
DATED : NOVEMBER 23, 1999
INVENTOR(S) : HAMILTON, ET AL.

It is certified that error appears in the above-identified patent and that said Letters Patent is hereby corrected as shown below:

On title page, item [73] correct Assignee name: --GPI NIL Holdings, Inc., Wilmington, Del.--

Page 2, right column, line 6, the page citation "5031.3" should read: --5031-5033.--

Column 6, line 60: delete "trifluoromethyl hydroxy" and insert --trifluoromethyl, hydroxy--.

Column 7, Table I, compound 40, column $R_1$: delete "1,5-Diphenyl-3-sentyl" and insert --1,5-Diphenyl-3-pentyl--.

Column 7, Table I, compound 41, column $R_1$: delete "1,5-Diphenyl-3-sentyl" and insert --1,5-Diphenyl-3-pentyl--.

Column 8, line 66: replace "(5phenylpentanoyl)" with --(5-phenylpentanoyl)--.

Column 9, line 14: replace "(2cyclopentyl-1,2-dioxoethyl)" with --(2-cyclopentyl-1,2-dioxoethyl)--.

Column 9, lines 32-33: replace "(2-cyclohexyl-1,2-dioxopentyl)" with --(2-cyclohexyl-1,2-dioxoethyl)--.

Column 9, line 52: replace "(2S)-1--(3,3-dimethyl" with --(2S)-1-(3,3-dimethyl--.

UNITED STATES PATENT AND TRADEMARK OFFICE
CERTIFICATE OF CORRECTION

PATENT NO. : 5,990,131
DATED : NOVEMBER 23, 1999
INVENTOR(S) : HAMILTON, ET AL.

It is certified that error appears in the above-identified patent and that said Letters Patent is hereby corrected as shown below:

Column 10, lines 1-2: replace "(3,3-dimethyl-2oxopentanoyl)" with --(3,3-dimethyl-2-oxopentanoyl)--.

Column 10, lines 28-29: replace "2-({1-oxo-6-phenyl}-butyl-1-(3,3-dimethyl-1,2-dioxobutyl)pyrrolidine" with --2-(1-oxo-6-phenyl)-hexyl-1-(2-cyclohexyl-1,2-dioxoethyl)piperidine--.

Column 10, lines 30-31: delete the text in its entirety.

Column 10, line 63: delete "$(Ar_1)n$" and insert --$(Ar_1)_n$,--.

Column 15, line 34: replace "(2S)-2-(1-oxo-5-phenyl-1-pentyl" with --(2S)-2-(1-oxo-5-phenyl)-1-pentyl--.

Column 15, line 67: replace "$CH_2C_{12}$" with --$CH_2Cl_2$--.

Column 16, line 12: replace "(2S)-2-({1-oxo-5-ohenyl}" with --(2S)-2-{1-oxo-5-phenyl}--.

Column 17, line 24: replace "$CH_2C_{12}$" with --$CH_2Cl_2$--.

Column 17, line 29: replace "$CH_2C_{12}$" with --$CH_2Cl_2$--.

Column 17, line 35: replace "j=7.5" with --J=7.5--.

Column 17, line 36: replace "j=7.4" with --J=7.4--.

UNITED STATES PATENT AND TRADEMARK OFFICE
CERTIFICATE OF CORRECTION

PATENT NO. : 5,990,131
DATED : NOVEMBER 23, 1999
INVENTOR(S) : HAMILTON, ET AL.

It is certified that error appears in the above-indentified patent and that said Letters Patent is hereby corrected as shown below:

Column 18, line 33: replace "$CH_2C_{12}$" with --$CH_2Cl_2$--.

Column 23, line 21: replace "claim 15" with --claim 10--.

Column 26, line 5: replace "3-(3-(Trifluoromethyl)phenyl)propyl" with --3-[3-(Trifluoromethyl)phenyl]propyl--.

Column 27, line 56: replace "3-(4-(Trifluoromethyl)phenyl)" with --3-[4-(Trifluoromethyl)phenyl]--.

Column 28, line 42: replace "piperidine-carbothioate" with --piperidinecarbothioate--.

Signed and Sealed this

Twenty-seventh Day of February, 2001

Attest:

NICHOLAS P. GODICI

Attesting Officer

Acting Director of the United States Patent and Trademark Office